US012758183B2

(12) United States Patent
Jiao et al.

(10) Patent No.: US 12,758,183 B2
(45) Date of Patent: Oct. 13, 2026

(54) ULTRASOUND DEVICE AND ULTRASOUND IMAGING METHOD

(71) Applicant: SHENZHEN MINDRAY BIO-MEDICAL ELECTRONICS CO., LTD., Shenzhen (CN)

(72) Inventors: Jiaming Jiao, Shenzhen (CN); Shuo Liu, Shenzhen (CN); Muqing Lin, Shenzhen (CN); Haina Yang, Shenzhen (CN); Shuaifu Li, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 19/231,412

(22) Filed: Jun. 6, 2025

(65) Prior Publication Data

US 2025/0375189 A1 Dec. 11, 2025

(30) Foreign Application Priority Data

Jun. 7, 2024 (CN) ......................... 202410744368.2

(51) Int. Cl.

*A61B 8/12* (2006.01)
*A61B 8/00* (2006.01)
*A61B 8/08* (2006.01)

(52) U.S. Cl.

CPC .............. *A61B 8/12* (2013.01); *A61B 8/0883* (2013.01); *A61B 8/429* (2013.01); *A61B 8/4444* (2013.01); *A61B 8/467* (2013.01); *A61B 8/54* (2013.01)

(58) Field of Classification Search

CPC ........................................................ A61B 8/12
See application file for complete search history.

(56) References Cited

U.S. PATENT DOCUMENTS

| | | | | |
|---|---|---|---|---|
| 6,425,865 | B1 * | 7/2002 | Salcudean | A61B 34/32 600/437 |
| 11,653,889 | B2 * | 5/2023 | Popovic | G16H 50/30 600/443 |
| 11,918,404 | B2 * | 3/2024 | Popovic | A61B 1/00006 |
| 12,533,016 | B2 * | 1/2026 | Gafford | A61B 1/0055 |
| 2005/0043629 | A1 | 2/2005 | Rabiner | |
| 2008/0033295 | A1 | 2/2008 | Matsumura | |

(Continued)

FOREIGN PATENT DOCUMENTS

| | | | |
|---|---|---|---|
| CN | 102933254 | A | 2/2013 |
| CN | 106102592 | A | 11/2016 |

(Continued)

*Primary Examiner* — Colin T. Sakamoto
(74) *Attorney, Agent, or Firm* — Syncoda LLC; Feng Ma

(57) ABSTRACT

Disclosed are an ultrasound device and an ultrasound imaging method, including: controlling an ultrasound probe to perform transmission of ultrasound waves and reception of ultrasound echoes to obtain ultrasound echo signals that are used to generate an ultrasound image, wherein the ultrasound probe is guided into a patient's cavity body and in a contact state with a biological tissue that forms the cavity body; and after a first function key is triggered, at least controlling execution of a disengagement function. With the introduction of a first function key, the operation of moving away the ultrasound probe with a single keystroke can be completed by an operator, transitioning the ultrasound probe from a contact state to a non-contact state with the tissue.

20 Claims, 7 Drawing Sheets

(56) References Cited

U.S. PATENT DOCUMENTS

| | | | | |
|---|---|---|---|---|
| 2017/0135818 | A1 | 5/2017 | Oren | |
| 2018/0085090 | A1 | 3/2018 | In-Jeong | |
| 2020/0008651 | A1* | 1/2020 | Popovic | A61B 8/06 |
| 2020/0359997 | A1 | 11/2020 | Sujith | |
| 2023/0010773 | A1 | 1/2023 | Arkadiusz | |
| 2023/0120013 | A1 | 4/2023 | Sakie | |
| 2023/0248330 | A1* | 8/2023 | Popovic | A61B 6/5217<br>600/443 |

FOREIGN PATENT DOCUMENTS

| | | | |
|---|---|---|---|
| CN | 110801200 | A | 2/2020 |
| CN | 114126493 | A | 3/2022 |
| CN | 114828753 | A | 7/2022 |
| DE | 10058370 | A1 | 6/2002 |

* cited by examiner

ULTRASOUND DEVICE AND ULTRASOUND IMAGING METHOD

CROSS-REFERENCE TO RELATED APPLICATION

This application claims priority to Chinese patent Application No. 202410744368.2 filed on Jun. 7, 2024, the disclosure of which is hereby incorporated by reference in its entirety.

TECHNICAL FIELD

The present disclosure relates to the field of ultrasound imaging, in particular to ultrasound devices and ultrasound imaging methods.

BACKGROUND OF THE DISCLOSURE

Ultrasound imaging technology enables the imaging of numerous organs or tissues within a human body, assisting doctors in making diagnosis. This technology utilizes ultrasound waves to scan a human body's tissues and organs, receiving and processing reflected signals to obtain images of corresponding regions. Due to its advantages of non-invasive, low cost and high real-time performance, ultrasound imaging has gradually emerged as the most widely used and frequently utilized imaging modality in medical imaging examinations.

In some situations, it is necessary to insert an ultrasound probe into a patient's body cavity to achieve better imaging results. Taking a transesophageal echocardiography (TEE) probe as an example; it can be used preoperatively or intraoperatively to observe cardiac structures and monitor cardiac function. Specifically, a doctor may guide the TEE probe into a patient's esophagus or stomach, and, to obtain better imaging results, position it in close contact with the esophageal or gastric wall for imaging. However, prolonged contact between the probe and the esophageal or gastric wall may compress tissues, causing damage. Consequently, the TEE probe is moved away occasionally (particularly when real-time imaging is temporarily not needed). Typically, this requires manipulating multiple buttons and/or knobs to move the TEE probe; and in scenarios such as during surgery, such retraction operations may be repeated multiple times. This not only makes the procedure complex and time-consuming but also prone to errors, potentially causing trauma to the patient.

SUMMARY OF THE DISCLOSURE

In view of the aforementioned issues, the present disclosure provides ultrasound devices and ultrasound imaging methods, as described in detail below.

According to a first aspect of the present disclosure, an ultrasound device provided in some embodiments may include:

- an ultrasound probe, configured to perform transmission of ultrasound waves and reception of ultrasound echoes to obtain ultrasound echo signals;
- a guidance member, comprising a guide body and a distal portion, wherein the ultrasound probe is disposed at the distal portion, and the guide body is configured to guide the ultrasound probe at the distal portion into a patient's body cavity;
- a drive mechanism, configured to drive the ultrasound probe to move within the body cavity;

- a first function key, capable of being triggered by an operator to execute a first function; and
- a controller; wherein:
- when the ultrasound probe is guided into the body cavity and in a contact state with a biological tissue that forms the body cavity, the ultrasound probe performs the transmission of ultrasound waves and the reception of ultrasound echoes to obtain the ultrasound echo signals, wherein the ultrasound echo signals are used to generate an ultrasound image;
- when the first function key is triggered, the controller is configured to control execution of the first function and a disengagement function; wherein the first function is different from the disengagement function, and the disengagement function comprises the controller controlling the drive mechanism to drive the ultrasound probe to perform a disengagement motion so as to transition from the contact state to a non-contact state with the biological tissue.

In some embodiments, the ultrasound probe has a front side and a rear side that is opposite to the front side, wherein the front side of the ultrasound probe comprises a contact region configured to contact the biological tissue, and the disengagement motion comprises a backward motion of the ultrasound probe in a front-rear direction defined by the front side and the rear side.

In some embodiments, the backward motion comprises a linear and/or rotational backward movement of the ultrasound probe in the front-rear direction.

In some embodiments, when the first function key is triggered, the controller is further configured to control execution of a stop transmission-reception function, wherein the stop transmission-reception function comprises the controller controlling the ultrasound probe to stop the transmission of ultrasound waves and the reception of ultrasound echoes.

In some embodiments, when the first function key is triggered, the controller is further configured to determine whether the ultrasound probe is in the contact state with the biological tissue:

- when the ultrasound probe is in the contact state with the biological tissue, the controller is further configured to execute the disengagement function; and
- when the ultrasound probe is in the non-contact state with the biological tissue,
- the controller is further configured to prohibit the disengagement function.

In some embodiments, the first function key is any one of the following:

- a freeze key, wherein the first function is to freeze the ultrasound image;
- a sleep key, wherein the first function is to switch from an operative mode to a sleep mode;
- a lock key, wherein the first function is to switch from the operative mode to a locked mode; and
- a save key, wherein the first function is to save a current ultrasound image.

In some embodiments, the ultrasound device further comprises a second function key; when the second function key is triggered by the operator, the controller is further configured to control execution of a reset function; wherein the reset function comprises the controller controlling the drive mechanism to drive the ultrasound probe to perform a reset motion so as to transition from the non-contact state to the contact state with the biological tissue.

In some embodiments, when the second function key is triggered by the operator, the controller is further configured to control execution of a transmission-reception function, wherein the transmission-reception function comprises the controller controlling the ultrasound probe to resume the transmission of ultrasound waves and the reception of ultrasound echoes.

In some embodiments, when the second function key is triggered, the controller is further configured to control execution of a second function, wherein the second function is different from the reset function.

In some embodiments, the second function is a function opposite to the first function.

In some embodiments, the second function key is any one of the following: an unfreeze key, wherein the second function is to unfreeze the ultrasound image;

a wake-up key, wherein the second function is to switch from the sleep mode to the operative mode; and an unlock key, wherein the second function is to switch from the locked mode to the operative mode.

In some embodiments, the controller controlling the drive mechanism to drive the ultrasound probe to perform the reset motion so as to transition from the non-contact state to the contact state with the biological tissue comprises:

the controller controlling the drive mechanism to drive the ultrasound probe to perform the reset motion until the ultrasound probe reaches a predetermined position; wherein the predetermined position comprises any one of the following:

an initial position of the ultrasound probe relative to the biological tissue before performing the disengagement motion;

a position of the ultrasound probe where a similarity between an ultrasound image of said position and a predetermined sectional image is greater than a predetermined similarity threshold;

a position of the ultrasound probe where a quality metric of the generated ultrasound image is greater than a predetermined quality threshold;

a position of the ultrasound probe where both a similarity between an ultrasound image of said position and the predetermined sectional image is greater than a predetermined similarity threshold, and a quality metric of the ultrasound image is greater than a predetermined quality threshold; and a position of the ultrasound probe where a contact force between the ultrasound probe and the biological tissue satisfies a predetermined pressure condition.

In some embodiments, the controller controlling the drive mechanism to drive the ultrasound probe to perform the reset motion until the ultrasound probe reaches the predetermined position comprises:

the controller determining whether the ultrasound probe has moved to the initial position based on a real-time ultrasound image and at least one pre-stored target ultrasound image;

wherein the at least one pre-stored target ultrasound image comprises: an ultrasound image captured by the ultrasound probe at the initial position; or a plurality of ultrasound images on different sections captured by the ultrasound probe while controlled by the controller to move within a predetermined range prior to performing the disengagement motion.

In some embodiments, the controller controlling the drive mechanism to drive the ultrasound probe to perform the reset motion until the ultrasound probe reaches the predetermined position further comprises:

the controller controlling the drive mechanism to drive the ultrasound probe to perform the reset motion so as to move to the predetermined position based at least on the real-time ultrasound image, wherein the controller is further configured to calculate a reset motion parameter based on the at least one pre-stored target ultrasound image and the real-time ultrasound image, and to control the drive mechanism to drive the ultrasound probe to perform the reset motion based at least on the reset motion parameter;

wherein the at least one pre-stored target ultrasound image comprises: an ultrasound image captured by the ultrasound probe at the initial position; or a plurality of ultrasound images on different sections captured by the ultrasound probe while controlled by the controller to move within a predetermined range prior to performing the disengagement motion.

In some embodiments, the controller controlling the drive mechanism to drive the ultrasound probe to perform the reset motion so as to transition from the non-contact state to the contact state with the biological tissue comprises:

the controller obtaining a disengagement motion parameter of the drive mechanism during the disengagement motion of the ultrasound probe, and calculating to obtain a reset motion parameter that is opposite to the disengagement motion parameter; and the controller controlling the drive mechanism to drive the ultrasound probe to perform the reset motion based at least on the reset motion parameter.

In some embodiments, the reset motion comprises a forward motion of the ultrasound probe in a front-rear direction defined by the front side and the rear side.

In some embodiments, the forward motion comprises a linear and/or rotational forward movement of the ultrasound probe in the front-rear direction In some embodiments, the ultrasound probe is further provided with a pressure sensor, the pressure sensor is configured to convert detected pressure into electrical signals for measuring a contact force between the ultrasound probe and the biological tissue;

or, the controller is further configured to calculate a contact force between the ultrasound probe and the biological tissue based on the ultrasound image.

In some embodiments, the controller calculating the contact force between the ultrasound probe and the biological tissue based on the ultrasound image comprises:

the controller extracting an image of a shallow tissue from the ultrasound image, determining a deformation of the shallow tissue in a depth range of ultrasound imaging based on the shallow tissue image, and calculating the contact force based on the deformation.

In some embodiments, the controller is further configured to determine whether the ultrasound probe is in the contact state or the non-contact state with the biological tissue based on the contact force;

and/or, the controller is further configured to obtain the contact force and determine whether the contact force is greater than a first predetermined pressure threshold, wherein when the contact force is greater than a first predetermined pressure threshold, the controller is further configured to control the drive mechanism to stop movement of the ultrasound probe and/or to issue an alarm.

In some embodiments, the first function is different from a function for driving the ultrasound probe to move, or the first function is independent of the function for driving the ultrasound probe to move, or the first function excludes the function for driving the ultrasound probe to move;

and/or, the second function is different from the function for driving the ultrasound probe to move, or the second function is independent of the function for driving the ultrasound probe to move, or the second function excludes the function for driving the ultrasound probe to move.

In some embodiments, the ultrasound probe is a transesophageal echocardiography (TEE) probe; the body cavity is an esophagus or a stomach of the patient; and the guide body is configured to guide the TEE probe disposed at the distal portion into the esophagus or the stomach;

wherein, when the TEE probe is guided into the esophagus or the stomach and in the contact state with an inner wall tissue of the esophagus or the stomach, the TEE probe is configured to transmit the ultrasound waves to the heart of the patient and receive the ultrasound echoes to obtain the ultrasound echo signals that are used to generate a transesophageal echocardiogram.

According to a second aspect of the present disclosure, an ultrasound device provided in some embodiments may include:

an ultrasound probe, configured to perform transmission of ultrasound waves and reception of ultrasound echoes to obtain ultrasound echo signals;

a guidance member, comprising a guide body and a distal portion, wherein the ultrasound probe is disposed at the distal portion, and the guide body is configured to guide the ultrasound probe at the distal portion into a patient's body cavity;

a drive mechanism, configured to drive the ultrasound probe to move within the body cavity;

a first function key, capable of being triggered by an operator to execute a disengagement function and a stop transmission-reception function; and a controller; wherein:

when the ultrasound probe is guided into the body cavity and in a contact state with a biological tissue that forms the body cavity, the ultrasound probe performs the transmission of ultrasound waves and the reception of ultrasound echoes to obtain the ultrasound echo signals, wherein the ultrasound echo signals are used to generate an ultrasound image;

when the first function key is triggered, the controller is configured to execute the disengagement function and the stop transmission-reception function, wherein the disengagement function comprises the controller controlling the drive mechanism to drive the ultrasound probe to perform a disengagement motion so as to transition from the contact state to a non-contact state with the biological tissue, and the stop transmission-reception function comprising the controller controlling the ultrasound probe to stop the transmission of ultrasound waves and the reception of ultrasound echoes.

In some embodiments, the ultrasound probe comprises a front side and a rear side that is opposite to the front side, the front side of the ultrasound probe comprises a contact region configured to contact the biological tissue, wherein the disengagement motion comprises a backward motion of the ultrasound probe in a front-rear direction defined by the front side and the rear side.

In some embodiments, the backward motion comprises a linear and/or rotational backward movement of the ultrasound probe in the front-rear direction.

In some embodiments, when the first function key is triggered, the controller is further configured to control execution of the first function; wherein the first function is different from the disengagement function.

In some embodiments, the first function key is any one of the following:

a freeze key, wherein the first function is to freeze the ultrasound image;

a sleep key, wherein the first function is to switch from an operative mode to a sleep mode;

a lock key, wherein the first function is to switch from the operative mode to a locked mode; and a save key, wherein the first function is to save a current ultrasound image.

In some embodiments, the ultrasound device further comprises a second function key; when the second function key is triggered by the operator, the controller is further configured to control execution of a reset function, wherein the reset function comprises the controller controlling the drive mechanism to drive the ultrasound probe to perform a reset motion so as to transition from the non-contact state to the contact state with the biological tissue.

In some embodiments, when the second function key is triggered by the operator, the controller is further configured to control execution of a transmission-reception function, wherein the transmission-reception function comprises the controller controlling the ultrasound probe to resume the transmission of ultrasound waves and the reception of ultrasound echoes.

In some embodiments, when the second function key is triggered, the controller is further configured to control execution of a second function, wherein the second function is different from the reset function.

In some embodiments, the second function is a function opposite to the first function.

In some embodiments, wherein the second function key is any one of the following:

an unfreeze key, wherein the second function is to unfreeze the ultrasound image;

a wake-up key, wherein the second function is to switch from the sleep mode to the operative mode; and an unlock key, wherein the second function is to switch from the locked mode to the operative mode.

In some embodiments, the controller controlling the drive mechanism to drive the ultrasound probe to perform the reset motion so as to transition from the non-contact state to the contact state with the biological tissue comprises:

the controller controlling the drive mechanism to drive the ultrasound probe to perform the reset motion until the ultrasound probe reaches a predetermined position; wherein the predetermined position comprises any one of the following:

an initial position of the ultrasound probe relative to the biological tissue before performing the disengagement motion;

a position of the ultrasound probe where a similarity between an ultrasound image of said position and a predetermined sectional image is greater than a predetermined similarity threshold;

a position of the ultrasound probe where a quality metric of the generated ultrasound image is greater than a predetermined quality threshold;

a position of the ultrasound probe where both a similarity between an ultrasound image of said position and a predetermined sectional image is greater than a predetermined similarity threshold, and a quality metric of the ultrasound image is greater than a predetermined quality threshold; and a position of the ultrasound probe where a contact force between the ultrasound probe and the biological tissue satisfies a predetermined pressure condition.

In some embodiments, wherein the controller controlling the drive mechanism to drive the ultrasound probe to perform the reset motion until the ultrasound probe reaches the predetermined position comprises:

the controller determining whether the ultrasound probe has moved to the initial position based on a real-time ultrasound image and at least one pre-stored target ultrasound image;

wherein the at least one pre-stored target ultrasound image comprises: an ultrasound image captured by the ultrasound probe at the initial position; or a plurality of ultrasound images on different sections captured by the ultrasound probe while controlled by the controller to move within a predetermined range prior to performing the disengagement motion.

In some embodiments, the controller controlling the drive mechanism to drive the ultrasound probe to perform the reset motion until the ultrasound probe reaches the predetermined position further comprises:

the controller controlling the drive mechanism to drive the ultrasound probe to perform the reset motion so as to move to the predetermined position based at least on the real-time ultrasound image, wherein the controller is further configured to calculate a reset motion parameter based on the at least one pre-stored target ultrasound image and the real-time ultrasound image, and to control the drive mechanism to drive the ultrasound probe to perform the reset motion based at least on the reset motion parameter;

wherein the at least one pre-stored target ultrasound image comprises: an ultrasound image captured by the ultrasound probe at the initial position; or a plurality of ultrasound images on different sections captured by the ultrasound probe while controlled by the controller to move within a predetermined range prior to performing the disengagement motion.

In some embodiments, wherein the controller controlling the drive mechanism to drive the ultrasound probe to perform the reset motion so as to transition from the non-contact state to the contact state with the biological tissue comprises:

the controller obtaining a disengagement motion parameter of the drive mechanism during the disengagement motion of the ultrasound probe, and calculating to obtain a reset motion parameter that is opposite to the disengagement motion parameter; and the controller controlling the drive mechanism to drive the ultrasound probe to perform the reset motion based at least on the reset motion parameter.

In some embodiments, the reset motion comprises a forward motion of the ultrasound probe in a front-rear direction defined by the front side and the rear side.

In some embodiments, the forward motion comprises a linear and/or rotational forward movement of the ultrasound probe in the front-rear direction.

In some embodiments, the ultrasound probe is a TEE probe; the body cavity is an esophagus or a stomach of the patient; and the guide body is configured to guide the TEE probe disposed at the distal portion into the esophagus or the stomach;

wherein, when the TEE probe is guided into the esophagus or the stomach and in the contact state with an inner wall tissue of the esophagus or the stomach, the TEE probe is configured to transmit the ultrasound waves to the heart of the patient and receive the ultrasound echoes to obtain the ultrasound echo signals that are used to generate a transesophageal echocardiogram.

According to a third aspect of the present disclosure, an ultrasound device provided in some embodiments may include:

an ultrasound probe, configured to perform transmission of ultrasound waves and reception of ultrasound echo signals;

a guidance member, comprising a guide body and a distal portion, wherein the ultrasound probe is disposed at the distal portion, and the guide body is configured to guide the ultrasound probe at the distal portion into a patient's body cavity;

a drive mechanism, configured to drive the ultrasound probe to move within the body cavity;

one first function key, capable of being triggered in a first type by an operator to execute a disengagement function; and a controller; wherein:

when the ultrasound probe is guided into the body cavity and in a contact state with a biological tissue that forms the body cavity, the ultrasound probe performs the transmission of ultrasound waves and the reception of ultrasound echoes to obtain the ultrasound echo signals that are used to generate an ultrasound image; and when the first function key is triggered in the first type, the controller is configured to control execution of the disengagement function, wherein the disengagement function comprises the controller controlling the drive mechanism to drive the ultrasound probe to perform a disengagement motion, so as to transition from the contact state to a non-contact state with the biological tissue.

In some embodiments, the first-type trigger is a short press.

In some embodiments, the disengagement motion comprises a first movement range, the first movement range comprises a first linear displacement of not less than 2 centimeters and/or a first angular rotation of not less than 8 degrees.

In some embodiments, the ultrasound device further comprises a second function key; and when the second function key is triggered by the operator, the controller is further configured to control execution of a reset function, wherein the reset function comprises the controller to control the drive mechanism to drive the ultrasound probe to perform a reset motion, so as to transition from the non-contact state to the contact state with the biological tissue.

According to a fourth aspect of the present disclosure, an ultrasound imaging method provided in some embodiments may include:

controlling an ultrasound probe to perform transmission of ultrasound waves and reception of ultrasound echoes to obtain ultrasound echo signals that are used to generate an ultrasound image, wherein the ultrasound probe is guided into a patient's body cavity and in a contact state with a biological tissue that forms the body cavity; and controlling execution of a first function and a disengagement function when the first function key is triggered, wherein the first function is different from the disengagement function; and the disengagement function comprising: controlling the ultrasound probe to perform a disengagement motion so as to transition from the contact state to a non-contact state with the biological tissue.

In some embodiments, when the first function key is triggered, the controller also controls execution of a stop transmission-reception function; the stop transmission-reception function comprises: controlling the ultrasound probe to stop the transmission of ultrasound waves and the reception of ultrasound echoes.

According to a fifth aspect of the present disclosure, an ultrasound imaging method provided in some embodiments may include:

controlling an ultrasound probe to perform transmission of ultrasound waves and reception of ultrasound echoes to obtain ultrasound echo signals that are used to generate an ultrasound image, wherein the ultrasound probe is guided into a patient's body cavity and in a contact state with a biological tissue that forms the body cavity; and controlling execution of a disengagement function and a stop transmission-reception function when the first function key is triggered;

wherein the disengagement function comprises: controlling the ultrasound probe to perform a disengagement motion so as to transition from the contact state to a non-contact state with the biological tissue, and the stop transmission-reception function comprises: controlling the ultrasound probe to stop the transmission of ultrasound waves and the reception of ultrasound echoes.

In some embodiments, when the first function key is triggered, a first function is also performed, wherein the first function is different from the disengagement function.

In some embodiments, the first function key is any one of the following:

a freeze key, wherein the first function is to freeze the ultrasound image;

a sleep key, wherein the first function is to switch from an operative mode to a sleep mode;

a lock key, wherein the first function is to switch from the operative mode to a locked mode; and a save key, wherein the first function is to save a current ultrasound image.

In some embodiments, the ultrasound imaging method further comprises: controlling execution of a reset function when a second function key is triggered by the operator; wherein the reset function comprises: controlling the ultrasound probe to perform a reset motion so as to transition from the non-contact state to the contact state with the biological tissue.

In some embodiments, when the second function key is triggered by the operator, the controller is further configured to control execution of a transmission-reception function, wherein the transmission-reception function comprises the controller controlling the ultrasound probe to resume the transmission of ultrasound waves and the reception of ultrasound echoes.

In some embodiments, when the second function key is triggered, a second function is also controlled to execute, wherein the second function is different from the reset function.

In some embodiments, controlling the drive mechanism to drive the ultrasound probe to perform the reset motion so as to transition from the non-contact state to the contact state with the biological tissue comprises:

the controller controlling the drive mechanism to drive the ultrasound probe to perform the reset motion until the ultrasound probe reaches a predetermined position; wherein the predetermined position comprises any one of the following:

an initial position of the ultrasound probe relative to the biological tissue before performing the disengagement motion;

a position of the ultrasound probe where a similarity between an ultrasound image of said position and a predetermined sectional image is greater than a predetermined similarity threshold;

a position of the ultrasound probe where a quality metric of the generated ultrasound image is greater than a predetermined quality threshold;

a position of the ultrasound probe where both a similarity between an ultrasound image of said position and a predetermined sectional image is greater than a predetermined similarity threshold, and a quality metric of the ultrasound image is greater than a predetermined quality threshold; and a position of the ultrasound probe where a contact force between the ultrasound probe and the biological tissue satisfies a predetermined pressure condition.

In some embodiments, controlling the drive mechanism to drive the ultrasound probe to perform the reset motion until the ultrasound probe reaches the predetermined position comprises:

the controller determining whether the ultrasound probe has moved to the initial position based on a real-time ultrasound image and at least one pre-stored target ultrasound image;

wherein the at least one pre-stored target ultrasound image comprises: an ultrasound image captured by the ultrasound probe at the initial position; or a plurality of ultrasound images on different sections captured by the ultrasound probe while controlled by the controller to move within a predetermined range prior to performing the disengagement motion.

According to a sixth aspect of the present disclosure, an ultrasound imaging method provided in some embodiments may include:

controlling an ultrasound probe to perform transmission of ultrasound waves and reception of ultrasound echoes to obtain ultrasound echo signals that are used to generate an ultrasound image, wherein the ultrasound probe is guided into a patient's body cavity and in a contact state with a biological tissue that forms the body cavity; and controlling execution of a disengagement function when a first function key is triggered in a first type by an operator, wherein the disengagement function comprises controlling the ultrasound probe to perform a disengagement motion so as to transition from the contact state to a non-contact state with the biological tissue.

In some embodiments, the ultrasound imaging method further comprises: controlling execution of a reset function when a second function key is triggered by the operator; wherein the reset function comprises controlling the ultrasound probe to perform a reset motion so as to transition from the non-contact state with biological tissue to the contact state.

Based on the ultrasound devices and the ultrasound imaging methods described in the above embodiments, after the introduction of the first function key, the operator can complete the operation of moving away the ultrasound probe with a single keystroke, thereby transitioning the ultrasound probe from the contact state with the tissue to the non-contact state.

Based on the ultrasound devices and the ultrasound imaging methods described in the above embodiments, after the introduction of the second function key, the operator can complete restore the ultrasound probe from the disengaged state to its pre-disengagement state (i.e., the contact state) with a single keystroke.

DETAILED DESCRIPTION

Figure 1:
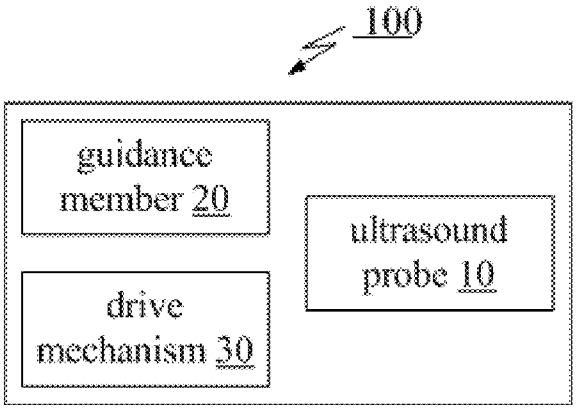
FIG. 1 is a schematic structural diagram of an ultrasound device in some embodiments.

Specific embodiments of the present disclosure will now be described in detail with reference to the accompanying drawings. Similar or related components in different embodiments are labeled with associated reference numerals. The following embodiments include detailed descriptions to facilitate understanding of the present disclosure. However, those skilled in the art will readily recognize that certain features may be omitted under specific circumstances or substituted by other components, materials, or methods. In some instances, certain operations related to the present disclosure are not explicitly described or illustrated herein. This intentional exclusion is intentional to avoid obscuring the core technical solutions of the present disclosure. For those skilled in the art, a complete understanding of these operations can be attained through the descriptions provided in this specification and general technical knowledge in the art.

Additionally, the features, operations, or characteristics described in the specification may be combined in any suitable manner to form various embodiments. Similarly, steps or actions in the method descriptions may be reordered or modified in ways that would be obvious to those skilled in the art. Therefore, the sequences presented in the specification and drawings are intended solely to clarify the description of specific embodiments and do not imply mandatory orderings, unless explicitly stated that a particular sequence is required.

The numerical designations assigned to components in this specification, such as ‘first,’ ‘second,’ or similar ordinal terms, serve solely to distinguish described objects and carry no inherent sequential or technical implications. Furthermore, the terms ‘connected’ and ‘coupled’ as used herein encompass both direct and indirect connection (coupling), unless explicitly stated otherwise.

FIG. 1 schematically illustrates the structure of an ultrasound device 100 in some embodiments of the present disclosure. The ultrasound device 100 comprises an ultrasound probe 10, a guidance member 20, and a drive mechanism 30, which will be described in detail below.

The ultrasound probe 10 is configured to perform transmission of ultrasound waves and reception of ultrasound echoes to obtain ultrasound echo signals. In some specific embodiments, the ultrasound probe 10 comprises a plurality of transducer elements configured to achieve mutual conversion between electrical pulse signals and ultrasound waves, thereby transmitting ultrasound waves to a target region and receiving ultrasound echoes reflected from tissues to acquire echo signals of the ultrasound waves (i.e., ultrasound echo signals). In some embodiments, the plurality of transducer elements included in the ultrasound probe 10 may be arranged in a row to form a linear array. In some embodiments, the plurality of transducer elements included in the ultrasound probe 10 are arranged in a two-dimensional matrix to form a planar array. The transducer elements are manufactured using, for example, piezoelectric crystals.

Figure 2:
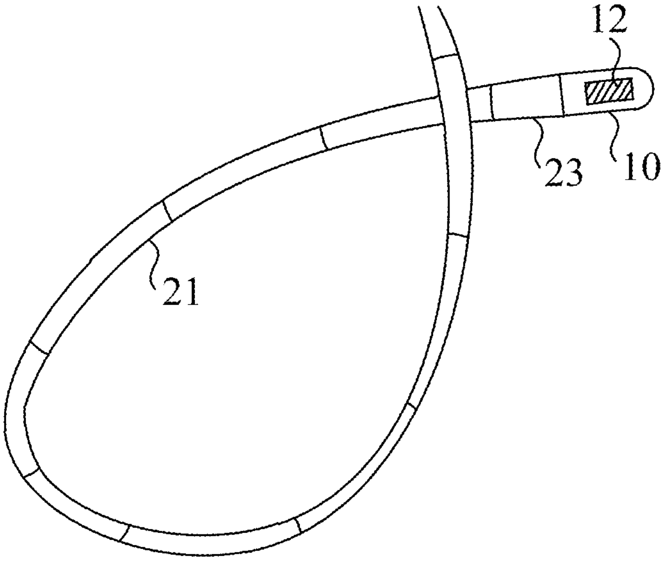
FIG. 2 is a schematic structural diagram of an ultrasound device in some embodiments.
Figure 3:
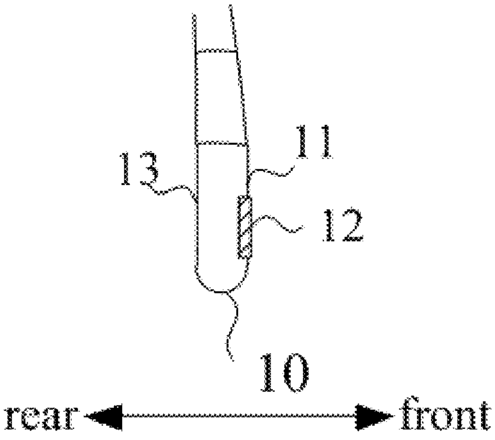
FIG. 3 is a schematic diagram of an ultrasound probe and its front-rear direction in some embodiments.

Referring to FIGS. 2 and 3, in some embodiments, the ultrasound probe 10 includes a front side 11 and a rear side 13 opposite to the front side. The front side 11 of the ultrasound probe 10 comprises a contact region 12 (shown as the region with black diagonal hatching in the figures) configured to be in contact with biological tissues. In other words, the side of the ultrasound probe 10 where the contact region 12 is located is defined as the front side 11, and the other side opposite to the front side 11 is defined as the rear side 13 of the ultrasound probe 10, thereby establishing a front-rear direction defined between the front side 11 to the rear side 13. FIG. 3 schematic illustrates a side view of the ultrasound probe 10, where the arrow indicates the front and rear directions. It should be noted that the front-rear direction defined by the front side 11 and rear side 13 is intrinsic to the ultrasound probe 10 itself, establishing a probe-defined coordinate system that is independent of absolute physical world orientations, such as east, south, west, or north. This will be further illustrated in subsequent descriptions.

The guidance member 20 includes a guide body 21 and a distal portion 23, wherein the ultrasound probe 10 is disposed at the distal portion 23, and the guide body 21 is configured to guide the ultrasound probe 10 at the distal portion 23 into a patient's body cavity. Generally, to achieve optimal imaging performance during operation of the ultrasound device 100, after the ultrasound probe 10 is guided into the body cavity, the contact region 12 of the ultrasound probe is configured to be in contact with biological tissue that forms the body cavity.

Figure 4:
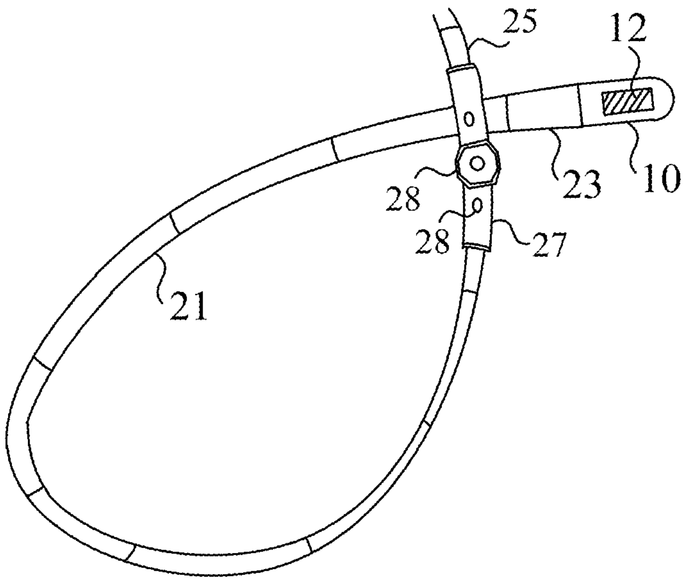
FIG. 4 is a schematic structural diagram of an ultrasound device in some embodiments.

Referring to FIG. 4, in some embodiments, the guidance member 20 further comprises a proximal portion 25 that is an end opposite to the distal portion 23. The distal portion 23 is the end configured to be inserted into a patient's body cavity, and the proximal portion 25 is the end proximate to an operator. In some examples, the guide body 21 and the distal portion 23 may be integrally formed or detachably coupled; similarly, the guide body 21 and the proximal portion 25 may be integrally formed or detachably coupled. The guide body 21 may be an elongated and flexible structure, thereby allowing it to be inserted into a patient's body to guide the ultrasound probe 10 at the distal portion 23 into the body cavity.

The drive mechanism 30 is configured to drive the ultrasound probe 10 to move within the body cavity. In some examples, the drive mechanism 30 is configured to drive the ultrasound probe 10 to perform one or more motions within the body cavity, including translation, pivoting, and rotation. Pivoting of the ultrasound probe 10 may be defined as angular displacement about a predetermined pivot point that may correspond to a location on the distal portion 23. Rotation of the ultrasound probe 10 may be defined as circumferential displacement about its own longitudinal axis (or the longitudinal axis of the distal portion 23), thereby orienting the contact region 12 of the ultrasound probe 10 toward different directions.

Figure 5:
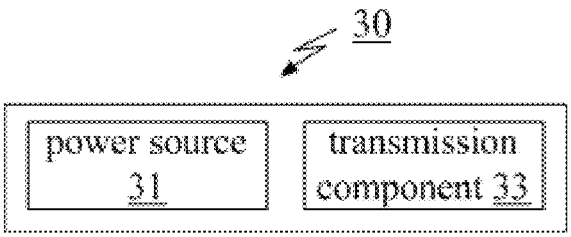
FIG. 5 is a schematic structural diagram of a drive mechanism in some embodiments.

Referring to FIG. 5, in some embodiments, the drive mechanism 30 may include a power source 31 and one or more transmission components 33. The power source 31 is configured to provide driving force, and it may be for example an electric motor. The transmission component 33 is configured to transmit the driving force to the ultrasound probe 10 so as to drive the ultrasound probe 10 to move.

In some examples, the guide body 21 defines an internal compartment housing the drive mechanism 30. The internal compartment may also accommodate cables for signal and data transmission with the ultrasound probe 10. Additionally, in some examples, the drive mechanism 30 may be partially disposed in the internal compartment or even entirely external to the guide body 21.

Figure 6:
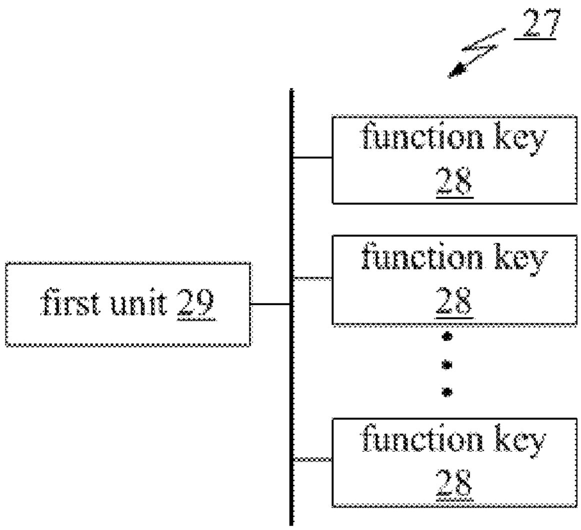
FIG. 6 is a schematic structural diagram of a operational handle in some embodiments.

To enable intuitive operator control of the ultrasound probe 10, an operational handle 27 may be disposed at the proximal portion 25 of the guidance member 20. FIG. 4 is an example. The operational handle 27 is configured for operator manipulation and comprises one or more function keys 28 (e.g., physical buttons, knobs, levers, trackballs, or touch-sensitive interfaces). It should be noted that the function keys 28 may be customized based on application requirements. In some examples, the operational handle 27 includes one or more function keys 28 (hereinafter referred to as "motion function keys") configured to regulate movement (e.g., translation or pivoting) of the ultrasound probe 10 within the body cavity through operator input. Referring to FIG. 6, in some embodiments, the operational handle 27 further comprises a first unit 29 incorporating control functions and/or data processing functions. In some examples, the first unit 29 is configured to generate control commands based on signals triggered by the function keys 28, thereby controlling the drive mechanism 30 or the ultrasound probe 10 to perform a corresponding function. In some examples, the first units 29 is also configured to receive signals or instructions from, for example, an ultrasound host 40 described below and generate corresponding control commands to control the drive mechanism 30 or the ultrasound probe 10 to perform a corresponding function. In some embodiments, the first unit 29 may include, but is not limited to, embedded electronic components such as a central processing unit (CPU), micro controller unit (MCU), field-programmable gate array (FPGA), or digital signal processor (DSP), which are configured to execute computer instructions and process data from associated software.

Figure 7:
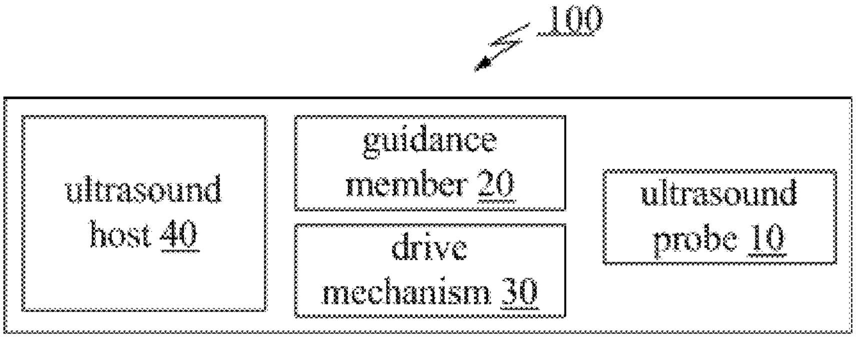
FIG. 7 is a schematic structural diagram of an ultrasound device in some embodiments.
Figure 8:
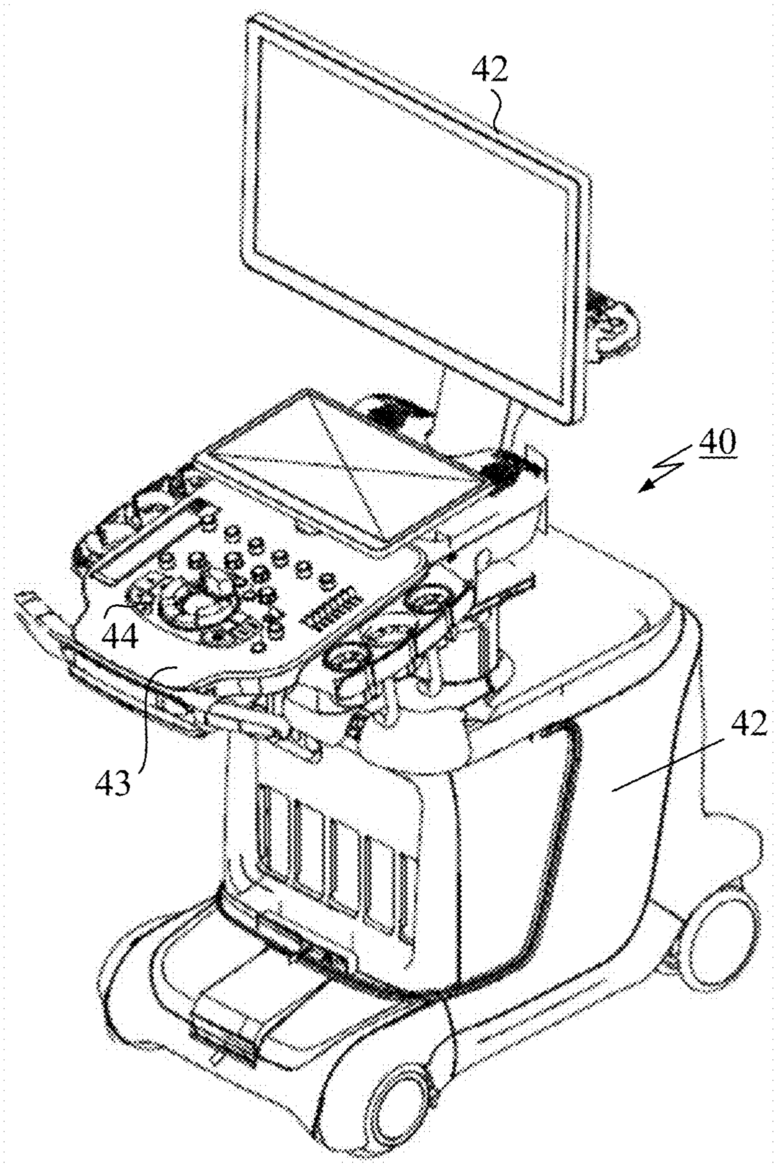
FIG. 8 is a schematic structural diagram of an ultrasound host in some embodiments.

Referring to FIG. 7, in some embodiments, the ultrasound device 100 may further include an ultrasound host 40 that is capable of receiving the ultrasound echo signals transmitted by the ultrasound probe 10 to generate ultrasound images. FIG. 8 illustrates an exemplary three-dimensional structure of the ultrasound host 40, which may include a second unit 42 with control and/or data processing functions and a display component 42. The second unit 42 is capable of processing the ultrasound echo signals to generate ultrasound images. The display component 42 is configured to display content, such as the ultrasound images. In some embodiments, the second unit 42 includes, but is not limited to, a CPU, MCU, FPGA, and DSP, which are configured to execute computer instructions and process data from computer software. In some examples, the ultrasound host 40 may also include an operation panel 43 that is configured to allow operator interaction and may comprise one or more function keys 44 (e.g., physical buttons, knobs, levers, trackballs, or touch-sensitive interfaces). It should be noted that the function keys 44 may be customized based on requirements. In some examples, the function keys 44 on the operation panel 43 may enable the operator to perform one or more of the following operations: setting ultrasound imaging modes; configuring ultrasound imaging parameters; freezing ultrasound images; unfreezing ultrasound images; switching the ultrasound device 100 between different states (e.g., operative mode, sleep mode, locked mode), controlling the operation of the ultrasound probe 10, and controlling the motion of the ultrasound probe 10.

In some examples, the guidance member 20 can be plugged into the ultrasound host 40, thereby enabling signal transmission and data transmission between the ultrasound host 40 and components such as the ultrasound probe 10.

The above is some description of the ultrasound device 100.

Figure 9:
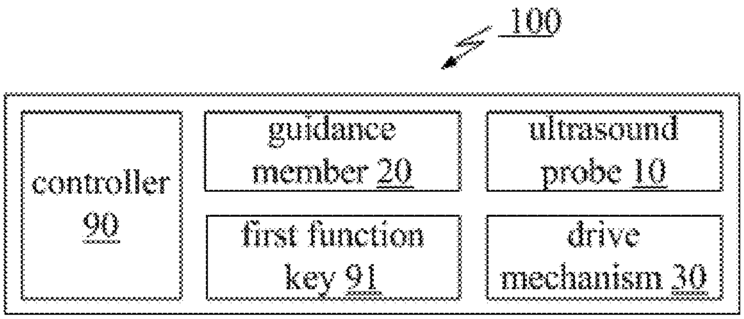
FIG. 9 is a schematic structural diagram of an ultrasound device in some embodiments.

As described above, to achieve improved imaging performance during the imaging process performed by the ultrasound device 100, after the ultrasound probe 10 is guided into a patient's body cavity, it is necessary that the contact region 12 of the probe be in a contact state with the biological tissue that forms the body cavity. However, prolonged contact of the ultrasound probe 10 with the patient's biological tissue may compress the tissue, potentially causing damage. Accordingly, the operator may move away the ultrasound probe 10 periodically (particularly when real-time observation of ultrasound imaging is temporarily unnecessary) to allow the ultrasound probe 10 to be in a non-contact state with the biological tissue that forms the body cavity. Typically, the operator need to manipulate multiple buttons and/or knobs (e.g., motion function keys 28 on the operational handle 27) to move the ultrasound probe 10, resulting in operationally complex and time-consuming procedures. To address these limitations, as shown in FIG. 9, in some embodiments, the ultrasound device 100 include a first function key 91 and a controller 90, as detailed below.

The controller 90 is a component configured to perform control functions and/or data processing operations. In some examples, the controller 90 may include, but is not limited to, devices such as a CPU, MCU, FPGA, and DSP, which are configured to execute computer instructions and process data from computer software. In some examples, the controller 90 may be disposed at the proximal portion 25 of the guidance member 50. For example, the controller 90 may be positioned within the operational handle 27. The operational handle 27 may incorporate the controller 90 that may be integrated with the first unit 29 or exist as a separate component. In other examples, the controller 90 may be disposed on a side of the ultrasound host 40. For instance, the controller 90 may be integrated into the ultrasound host 40. The ultrasound main unit 40 may also include the controller 90 that may be integrated with the second unit 42 or exist as a separate component.

The first function key 91 is configured to be actuated by the operator to execute associated functions. The first function key 91 may be in a form of, including, but not limited to, a physical button, a physical knob, a physical lever, a trackball, or a touch-sensitive key. In some specific embodiments, the first function key 91 may be implemented as a physical button. In some examples, the first function key 91 may be disposed at the proximal portion 25 of the guidance member 50. For instance, the first function key 91 may be a function key 28 on the operational handle 27. In other examples, the first function key 91 may be disposed on the side of the ultrasound host 40, such as a function key 44 on the operation panel 43 of the ultrasound host 40. Additionally, the first function key 91 may also be implemented as an operational control, such as an operational control displayed on a display component 42, which can be triggered by the operator through a click to execute the aforementioned associated functions.

A process may be as follows:

When the ultrasound probe 10 is guided into a patient's body cavity and in the contact state with the biological tissue that forms the body cavity, the ultrasound probe 10 performs transmission of ultrasound waves and reception of ultrasound echoes to obtain ultrasound echo signals. The ultrasound echo signals are used to generate an ultrasound image. For example, the first unit 42, the second unit 42, or the controller 90 processes the ultrasound echo signals to generate the ultrasound image. Alternatively, two or three of the first unit 42, the second unit 42, and the controller 90 may be cooperated, with each processing a subset of processing steps to ultimately generate the ultrasound image. When the first function key 91 is triggered, the controller 90 may control execution of a disengagement function. In some examples, when the first function key 91 is triggered, besides controlling the execution of the disengagement function, the controller 90 can control execution of a first function and/or a stop transmission-reception function. These operations are described in detail below.

In some embodiments, the disengagement function includes: the controller 90 controlling the drive mechanism 30 to drive the ultrasound probe 10 to perform a disengagement motion so as to transition from the contact state to the non-contact state with the biological tissue.

After the introduction of the first function key 91, the operator can complete the operation of moving away the ultrasound probe 10 with a single keystroke, transitioning the ultrasound probe 10 from the contact state with the tissue to the non-contact state.

Figure 10A:
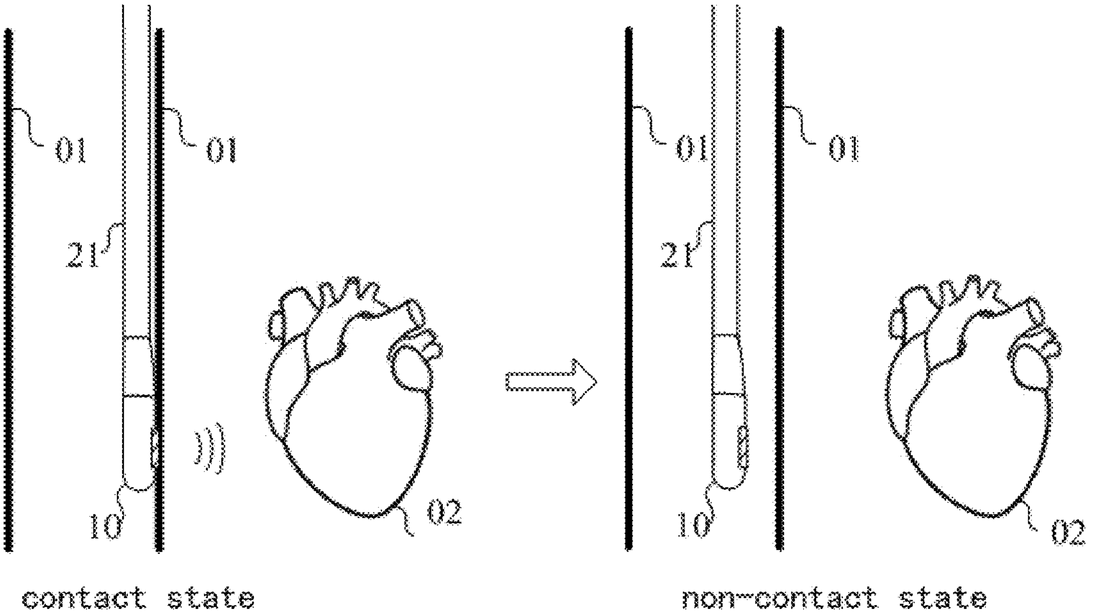
FIG. 10A is a schematic diagram of the linear backward movement of an ultrasound probe in some embodiments.
Figure 10B:
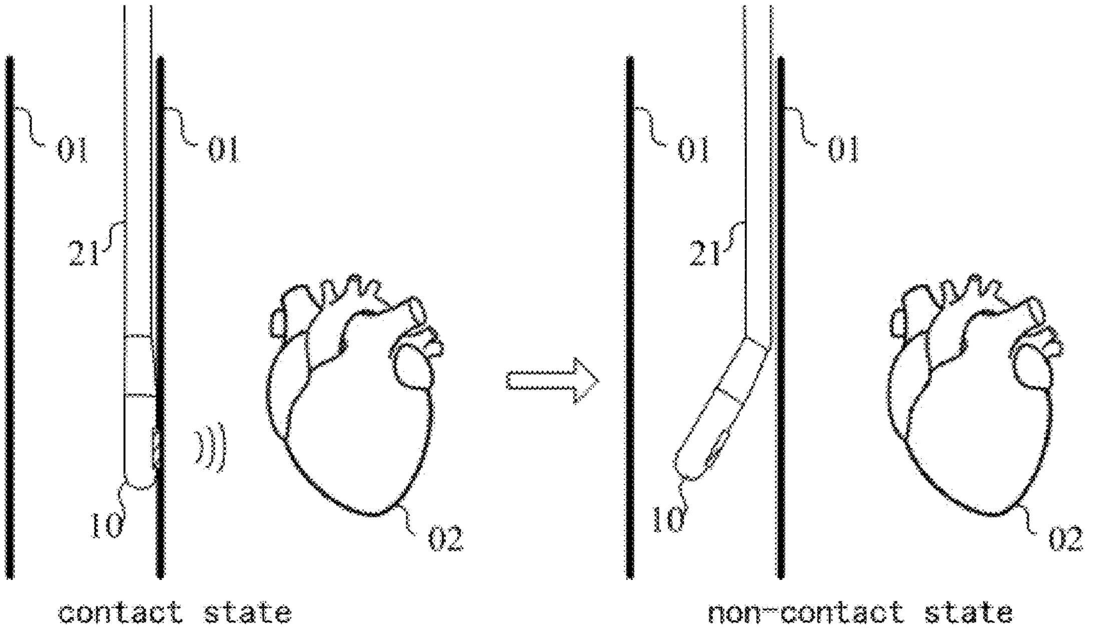
FIG. 10B is a schematic diagram of the rotational backward movement of an ultrasound probe in some embodiments.

In some examples, the disengagement motion includes a backward motion of the ultrasound probe 10 in a front-rear direction defined by the front side 11 and the rear side 13. In some examples, the backward motion may include a linear and/or rotational backward movement of the ultrasound probe 10 in the front-rear direction defined by the front side 11 and the rear side 13. FIG. 10A illustrates an example of the ultrasound probe 10 performing backward movement along the front-rear direction defined by the front side 11 and the rear side 13, consequently transitioning the ultrasound probe 10 from the contact state with the tissue to the non-contact state; and FIG. 10B illustrates an example of the ultrasound probe 10 performing a backward rotation within the front-rear direction defined by the front side 11 and the rear side 13, thereby also transitioning the ultrasound probe 10 from the contact state with the tissue to the non-contact state. In these figures, numeral 01 represents the wall of the body cavity, that is the biological tissue forming the body cavity, while numeral 02 indicates the target tissue for ultrasound imaging, such as a heart.

In some examples, the disengagement motion exhibits a first movement range that includes a first linear displacement and/or a first angular rotation that allow the ultrasound probe 10 to perform the disengagement motion so as to transition from the contact state to the non-contact state with the biological tissue. The first linear displacement refers to the amount of linear movement of the ultrasound probe 10, and the first angular rotation refers to the degree of rotation of the ultrasound probe 10. The first movement range may be configured by: determining a minimum motion required to transition the ultrasound probe 10 from the contact state to the non-contact state when the pressure between the ultrasound probe 10 and the biological tissue of the body cavity reaches a safety threshold, and then setting the first movement range to be greater than this minimum motion.

In some examples, the stop transmission-reception function comprises the controller 90 controlling the ultrasound probe 10 to stop the transmission of ultrasound waves and the reception of ultrasound echoes. In some examples, when the first function key 91 is triggered, it prompts the controller 90 to control execution of a stop transmission-reception function. The timing of the controller 90 controlling the ultrasound probe 10 to stop the transmission of ultrasound waves and the reception of ultrasound echoes may occur at various points during the disengagement motion, including its beginning, midst, or ending. Specifically, in some examples, the timing of the controller 90 controlling the ultrasound probe 10 to stop the transmission of ultrasound waves and the reception of ultrasound echoes may at the beginning of the disengagement motion.

In some examples, the first function is different from the disengagement function.

In some examples, the first function is distinct from a function for driving the movement of the ultrasound probe 10. In other examples, the first function is independent of the function for driving the movement of the ultrasound probe 10. In still other examples, the first function does not include the function for driving the movement of the ultrasound probe 10.

In some examples, the first function differs from the stop transmission-reception function.

In some examples, the first function is to freeze ultrasound images; and correspondingly, the first function key 91 may be configured as a freeze key. That is, the first function key 91 can serve as the freeze key, sharing the function of the original freeze key in the ultrasound device 100. When the function to freeze the ultrasound images is triggered, the controller 90 may also control the execution of the disengagement function. In some examples, the original freeze key in the ultrasound device 100 not only freezes the ultrasound images but also causes the ultrasound probe 10 to stop the transmission of ultrasound waves and the reception of ultrasound echoes; consequently, when the freeze key is triggered, the controller 90 only needs to additionally control the execution of the disengagement function. In other examples, the freeze function implemented by the original freeze key only freezes the ultrasound image without causing the ultrasound probe 10 to stop the transmission of ultrasound waves and the reception of ultrasound echoes;

consequently, when the freeze key is triggered, the controller 90 may further control the execution of the disengagement function and, optionally, the stop transmission-reception function. Furthermore, the first function key 91 and the original freeze key in the ultrasound device 100 can be two separate keys, wherein when the original freeze key is triggered, it can either freeze the ultrasound images, or freeze the ultrasound images and cause the ultrasound probe 10 to stop the transmission of ultrasound waves and the reception of ultrasound echoes; and when the first function key 91 is triggered, it can execute the disengagement function and the freeze function, or it can execute the disengagement function, the freeze function and the stop transmission-reception function.

In some examples, the first function is to switch from the operative mode to the sleep mode; correspondingly, the first function key 91 may be configured as a sleep key. That is, the first function key 91 can serve as the sleep key, sharing the function of the original sleep key in the ultrasound device 100. When the sleep function (i.e., switching the operative mode of the ultrasound device 100 to the sleep mode) is activated, the controller 90 may also control the execution of the disengagement function. In some examples, the original sleep key in the ultrasound device 100 may include allowing the ultrasound probe 10 to stop the transmission of ultrasound waves and the reception of ultrasound echoes; consequently, when the sleep key is triggered, the controller 90 only needs to additionally control the execution of the disengagement function. Furthermore, the first function key 91 and the original sleep key in the ultrasound device 100 may be two separate keys, wherein when the original sleep key in the ultrasound device 100 is triggered, it can activate the sleep function; and when the first function key 91 is triggered, it can execute the disengagement function and the sleep function, or it can execute the disengagement function, the sleep function and the stop transmission-reception function.

In some embodiments, the first function is to switch from the operative mode to the locked mode; and correspondingly, the first function key 91 may be configured as a lock key. That is, the first function key 91 can serve as the lock key, sharing the function of the original lock key in the ultrasound device 100. When the function to lock (i.e., switching the operative mode of the ultrasound device 100 to the locked mode) is activated, the controller 90 may also control the execution of the disengagement function. In some examples, the lock function realized by the original lock key in the ultrasound device 100 may or may not include the function of causing the ultrasound probe 10 to stop the transmission of ultrasound waves and the reception of ultrasound echoes; consequently, when the sleep key is triggered, the controller 90 at least needs to additionally control the execution of the disengagement function. Furthermore, the first function key 91 and the original lock key in the ultrasound device 100 may also be two separate keys; wherein the lock function may be executed when the original lock key in the ultrasound device 100 is triggered; and when the first function key 91 is triggered, it can execute the disengagement function and the lock function, or it can execute the disengagement function, the lock function and the stop transmission-reception function.

In some embodiments, the first function is to save a current ultrasound image; and correspondingly, the first function key 91 may be configured as a save key. That is, the first function key 91 can serve as the save key, sharing the function of the original save key in the ultrasound device 100. When executing saving the current ultrasound image, the controller 90 may also control the execution of the disengagement function, or the controller 90 may also control the execution of the disengagement function and the stop transmission-reception function. Furthermore, the first function key 91 and the original save key in the ultrasound device 100 may also be two separate keys; wherein when the original save key in the ultrasound device 100 is triggered, the function of saving the current ultrasound image may be executed; and when the first function key 91 is triggered, it can execute the function of saving the current ultrasound image and the disengagement function, or it can execute the function of saving the current ultrasound image, the disengagement function, and the stop transmission-reception function.

The first function key 91 may share the same function as an original function key in the ultrasound device 100, allowing the integration of the disengagement function into the original operation process of this original function key. For example, when the first function key 91 shares the same function as the freeze key, since the current ultrasound image is typically frozen by operators when using the freeze key and there is no need to continue real-time ultrasound imaging temporarily, the activation of the disengagement function via the freeze key may be to integrate the disengagement function into the original frozen image process, eliminating the need for operators to perform additional operations, such as using a motion function key, to move the ultrasound probe 10 away from the tissue wall.

In some embodiments, considering safety issues, when the first function key 91 is triggered, the controller 90 further determines whether the ultrasound probe 10 is in the contact state with the biological tissue. If the ultrasound probe 10 is in the contact state with the biological tissue, the controller 90 may control the execution of the disengagement function. Conversely, if the ultrasound probe 10 is in the non-contact state with the biological tissue, the controller 90 may prevent the execution of the disengagement function to avoid the potential scenario where the ultrasound probe 10 might inadvertently change from the non-contact state to the contact state, resulting in accidental damage to the biological tissue.

There are various ways to determine whether the ultrasound probe 10 is in the contact state with the biological tissue, for example, by using the contact force between the ultrasound probe 10 and the biological tissue, which will be further described below.

In some examples, the triggering of the first function key 91 may be a first type, such as a short press. In some examples, the first function key 91 may also be triggered upon being pressed or upon being released after being pressed. The first function key 91 may not cause the ultrasound device 100 to perform different functions or actions based on the duration of the press.

In some examples, the disengagement motion has a first movement range which includes a first linear displacement and/or a first angular rotation. The first linear displacement is not less than 2 centimeters, and the first angular rotation is not less than 8 degrees. By pressing or tapping the first function key 91, the disengagement motion can be activated, enabling immediate disengagement with a single keystroke disengagement, thereby avoiding excessive operation time or frequency.

The above are some descriptions of the first function key 91.

Figure 11:
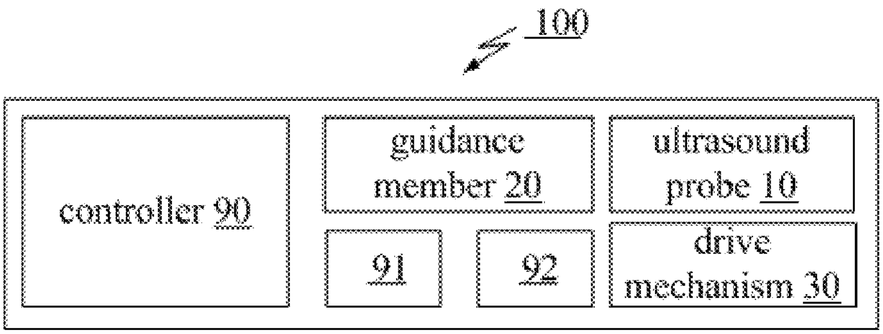
FIG. 11 is a schematic structural diagram of an ultrasound device in some embodiments.

When the ultrasound probe 10 is guided into the body cavity and is in the contact state with the biological tissue forming the body cavity, the ultrasound probe 10 performs the transmission of ultrasound waves and the reception of ultrasound echoes to obtain ultrasound echo signals that are used to generate an ultrasound image. In this case, upon triggering the first function key 91 by the operator, the controller 90 is activated to control execution of the disengagement function, causing the ultrasound probe 100 to perform the disengagement motion, transitioning it from the contact state to the non-contact state with the biological tissue. Subsequently, to quickly restore the ultrasonic probe 100 to its pre-disengagement state (such as the contact state before disengagement or even the operative mode before disengagement), a second function key 92 may be introduced, for example, FIG. 11 show an example.

The second function key 92 can be triggered by the operator to execute associated functions. The second function key 92 may be in various forms, including physical button, physical knob, physical lever, trackball, and touch-sensitive key. In some specific embodiments, the second function key 92 may be configured as a physical button. In some examples, the second function key 92 may be disposed at the proximal portion 25 of the guidance member 50. For instance, the second function key 92 may be a function key 28 on the operational handle 27. In other examples, the second function key 92 may be disposed on the side of the ultrasound host 40. For instance, the second function key 92 may be a function key 44 on the operation panel 43. Additionally, the second functional control 92 may be an operational control, such as an operational control displayed on the display component 42. By clicking this operational control by the operator, the functions associated with the second function key 92 can be executed.

In some embodiments, when the second function key 92 is triggered by the operator, the controller 90 may control the execution of a reset function. In some examples, when the second function key 92 is triggered, besides controlling the execution of the reset function, the controller 90 also controls the execution of the second function and/or the transmission-reception function. These functions will be described in detail below.

In some embodiments, the reset function comprises: the controller 90 controlling the drive mechanism 30 to drive the ultrasound probe 10 to perform the reset motion, so as to transition it from the non-contact state of the biological tissue to the contact state.

After the introduction of the second function key 92, the ultrasound probe 10 may be restored from the state it is in after disengagement back to the state it was in prior to disengagement with a single keystroke by the operator.

Figure 12A:
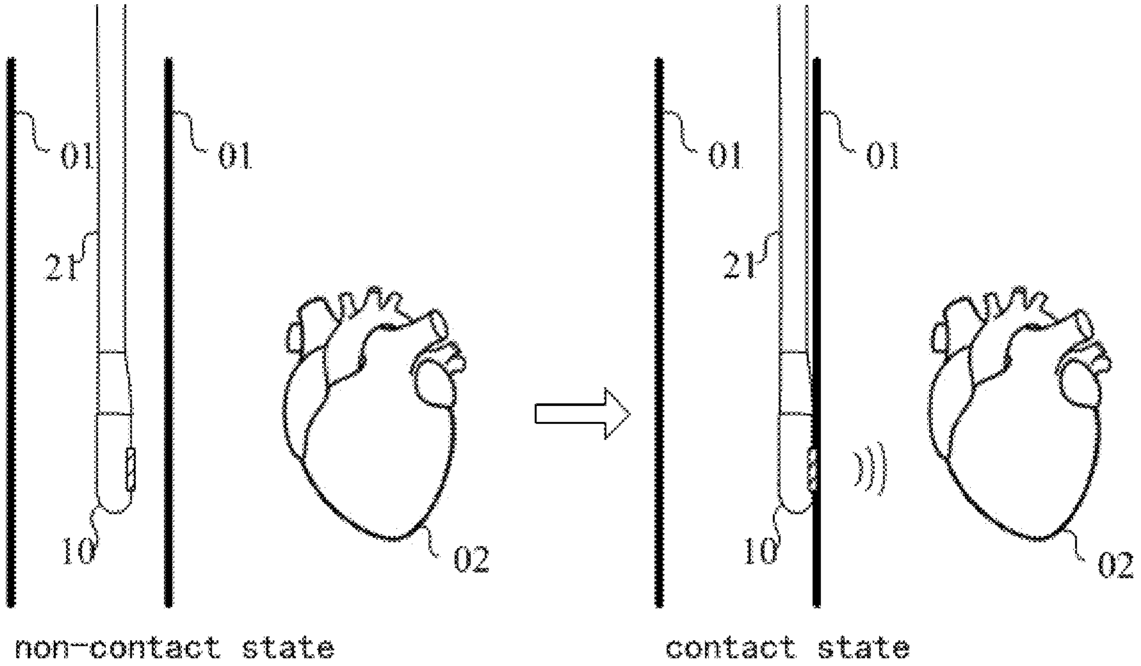
FIG. 12A is a schematic diagram of the linear forward movement of an ultrasound probe in some embodiments.
Figure 12B:
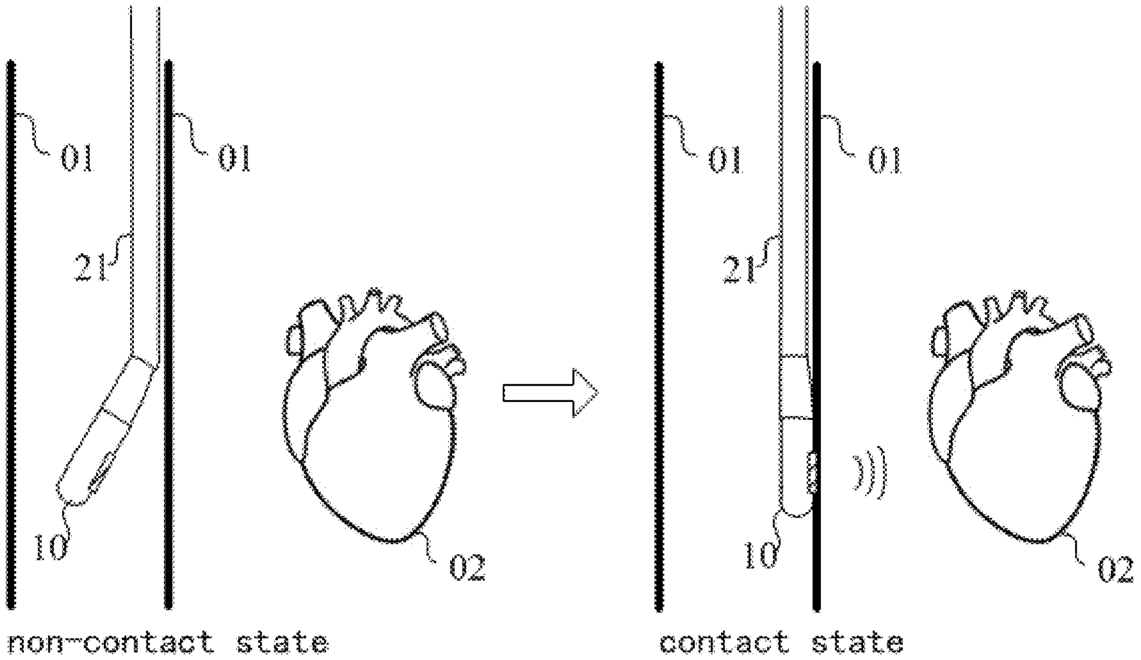
FIG. 12B is a schematic diagram of the rotational forward movement of an ultrasound probe in some embodiments.

In some examples, the reset motion comprises a forward motion of the ultrasound probe 10 in the front-rear direction defined by the front side 11 and the rear side 13. In some examples, the forward motion comprises a linear and/or rotational forward movement of the ultrasound probe 10 in the front-rear direction defined by the front side 11 and the rear side 13. FIG. 12A illustrates an example of the linear forward movement of the ultrasound probe 10 in the front-rear direction defined by the front side 11 and the rear side 13, thereby transitioning the ultrasound probe 10 from the non-contact state with the tissue to the contact state; and FIG. 12B illustrates an example of the rotational forward movement of the ultrasound probe 10 in the front-rear direction defined by the front side 11 and the rear side 13, thereby transitioning the ultrasound probe 10 from the non-contact state with the tissue to the contact state.

In some examples, the transmission-reception function comprises the controller 90 controlling the ultrasound probe 10 to resume the transmission of ultrasound waves and the reception of ultrasound echoes. In some examples, when second function key 92 is triggered, the controller 90 control the execution of the transmission-reception function; wherein the timing of the controller 90 controlling the ultrasound probe 10 to perform the transmission of ultrasound waves and the reception of ultrasound echoes may occur at various points during the reset motion, including its beginning, midst, or ending. Specifically, in some examples, the timing of the controller 90 controlling the ultrasound probe 10 to perform the transmission of ultrasound waves and the reception of ultrasound echoes may at the beginning of the reset motion.

In some examples, the second function is different from the reset function.

In some examples, the second function is different from the function for driving the ultrasound probe 10. In some examples, the second function is independent of the function for driving the ultrasound probe 10. In some examples, the second function does not include the function for driving the ultrasound probe 10.

In some examples, the second function is different from the transmission-reception function.

In some examples, the second function is contrary to or serves as a function opposite to the first function. For example, the first function is to freeze ultrasound images, and the second function is to unfreeze the ultrasound images. For another example, the first function is to switch from the operative mode to the sleep mode, and the second function is to switch from the sleep mode to the operative mode. For yet another example, the first function is to switch from the operative mode to the locked mode, and the second function is to switch from the locked mode to the operative mode. The following is a detailed explanation.

In some examples, the second function is to unfreeze ultrasound images; and correspondingly, the second function key 92 may be an unfreeze key. That is, the second function key 92 can serve as the unfreeze key, sharing the function of the original unfreeze key in the ultrasound device 100. When the function to unfreeze ultrasound images is activated, the controller 90 may also control the execution of the reset function. In some examples, besides unfreezing the ultrasound images, the original unfreeze key in the ultrasound device 100 may also allow the ultrasound probe 10 to resume the transmission of ultrasound waves and the reception of ultrasound echoes; consequently, when the unfreeze key is triggered, the controller 90 only needs to additionally control the execution of the reset function. In some examples, the unfreeze function implemented by the original unfreeze key only unfreezes the ultrasound image without causing the ultrasound probe 10 to resume the transmission of ultrasound waves and the reception of ultrasound echoes; consequently, when the unfreeze key is triggered, the controller 90 may further control the execution of the reset function and, optionally, the transmission-reception function. Furthermore, the second function key 92 and the original unfreeze key in the ultrasound device 100 can be two separate keys, wherein when the original unfreeze key is triggered, it can either unfreeze the ultrasound images, or unfreeze the ultrasound images and cause the ultrasound probe 10 to resume the transmission of ultrasound waves and the reception of ultrasound echoes; and when the second function key 92 is triggered, it can execute the reset function and the unfreeze function, or it can execute the reset function, the unfreeze function and the transmission-reception function.

In some examples, the second function is to switch from the sleep mode to the operative mode; and correspondingly, the second function key 92 may be a wake-up key. That is, the second function key 92 is the wake-up key, sharing the function of the original wake-up key in the ultrasound device 100. When the wake-up function (i.e., switching the ultrasound device 100 from the sleep mode to the operative mode) is activated, the controller 90 may further control the execution of the reset function. In some examples, the wake-up function implemented by the original wake-up key in the ultrasound device 100 may or may not include the function for allowing the ultrasound probe 10 to perform the transmission of ultrasound waves and the reception of ultrasound echoes; consequently, when the wake-up key is triggered, the controller 90 may at least need to additionally further control the execution of the reset function. Furthermore, the second function key 92 and the original wake-up key in the ultrasound device 100 may be two separate keys, wherein when the original wake-up key in the ultrasound device 100 is triggered, the wake-up function may be executed; and when the second function key 92 is triggered, it can execute the reset function and the wake-up function, or it can execute the reset function, the wake-up function and the transmission-reception function.

In some examples, the second function is to switch from the locked mode to the operative mode; and correspondingly, the second function key 92 may be configured as an unlock key. That is, the second function key 92 may serve as an unlock key, sharing the function of the original unlock key in the ultrasound device 100. When the unlock function (i.e., switching the ultrasound device 100 from the operative mode to unlock mode) is activated, the controller 90 may also control the execution of the reset function. In some examples, the unlock function realized by the original unlock key in the ultrasound device 100 may or may not include the function for allowing the ultrasound probe 10 to perform the transmission of ultrasound waves and the reception of ultrasound echoes; and accordingly, when the unlock key is triggered, the controller 90 may at least additionally further control the execution of the reset function. Furthermore, the second function key 92 and the original unlock key in the ultrasound device 100 may be two separate keys, wherein when the original unlock key is triggered, the unlock function may be executed; and when the second function key 92 is triggered, it may execute the reset function and the unlock function, or it can execute the reset function, the unlock function and the transmission-reception function.

The second function key 92 may share the same function as an original function key in the ultrasound device 100, allowing the integration of the reset function into the original operation process of this original function key. For example, when the second function key 92 shares the same function as the unfreeze key, since the current ultrasound image is typically unfrozen by operators when using the unfreeze key and there needs to resume real-time ultrasound imaging, the activation of the reset function via the unfreeze key may be to integrate the reset function into the original frozen image process, eliminating the need for operators to perform additional operations, such as using a motion function key, to move the ultrasound probe 10 towards the tissue wall.

The restoring of the ultrasound probe 10 from disengagement can be realized via the second function key 92 by the operator. In some embodiments, the controller 90 controls the drive mechanism 30 to drive the ultrasound probe 10 to perform the reset motion until the ultrasound probe 10 reaches a predetermined position. In some examples, the predetermined position may include any one of the following:

(1) an initial position of the ultrasound probe 10 relative to the biological tissue before performing the disengagement motion;

(2) a position of the ultrasound probe where a similarity between an ultrasound image of said position and a predetermined sectional image is greater than a predetermined similarity threshold;

(3) a position of the ultrasound probe where the quality metric of the generated ultrasound image is greater than a predetermined quality threshold;

(4) a position of the ultrasound probe where both a similarity between an ultrasound image of said position and a predetermined sectional image is greater than a predetermined similarity threshold, and a quality metric of the ultrasound image is greater than a predetermined quality threshold; and (5) a position of the ultrasound probe where the contact force between the ultrasound probe 10 and the biological tissue satisfied a predetermined pressure condition, such as being greater than a first pressure value and less than a second pressure value (with the second pressure value being greater the first pressure value, and the first pressure value being either zero or positive). In some examples, when the contact force between the ultrasound probe 10 and the biological tissue meets the predetermined pressure condition, the position where the ultrasonic probe 10 is located at this time enables the quality metric of the ultrasound image to be relatively high, such as exceeding a predetermined quality threshold.

Taking the position (1) as an example. The controller 90 controls the drive mechanism 30 to drive the ultrasound probe 10 to perform the reset motion until the ultrasound probe 10 reaches the position (1), that is, the initial position of the ultrasound probe 10 relative to the biological tissue before it performs the disengagement motion. In some embodiments, the controller 90 may determine whether the ultrasound probe 10 has moved to the position (1), i.e. the initial position, based on a real-time ultrasound image and at least one pre-stored target ultrasound image. The at least one pre-stored target ultrasound image may include an ultrasound image captured by the ultrasound probe 10 at the initial position, or, a plurality of ultrasound images on different sections captured by the ultrasound probe 10 within a predetermined range while controlled by the controller 90 prior to performing the disengagement motion.

In some embodiments, the controller 90 may control the drive mechanism 30 to drive the ultrasound probe 10 to perform the reset motion based on the real-time ultrasound images. The position of the ultrasound probe 10 may be characterized by the image features of the real-time ultrasound images. These image features may be the ultrasound image itself, a feature vector extracted from the ultrasound image, a recognized section type based on the ultrasound image, or a combination of any two or all three of these. The feature vector may be extracted using manually designed filters, including but not limited to one-dimensional filters, two-dimensional filters, or time-domain filters; alternatively, it may be extracted using machine learning algorithms, such as convolutional deep learning networks or self-attention-based deep learning networks. The section type of the ultrasound image may be obtained by processing the images using manually designed algorithms or machine learning algorithms; alternatively, key anatomical structures in the ultrasound image related to the human body may be first identified by an algorithm, and then mapped to the section type based on the identified key anatomical structures.

In some examples, the controller 90, based at least on the real-time ultrasound images, controls the drive mechanism 30 to drive the ultrasound probe to perform the reset motion so as to move to a predetermined position, such as any one of the aforementioned positions (1) to (5). In some examples, the controller 90 calculates a reset motion parameter based on at least one pre-stored target ultrasound image and the real-time ultrasound images, and controls the drive mechanism 30 based at least on the reset motion parameter to drive the ultrasound probe 10 to perform the reset motion. The at least one pre-stored target ultrasound image may include an ultrasound image captured by the ultrasound probe 10 at the initial position, or, a plurality of ultrasound images of different sections captured by the ultrasound probe 10 within a predetermined range while controlled by the controller 90 prior to performing the disengagement motion.

In some examples, the controller 90 obtains the disengagement motion parameter of the drive mechanism 30 that drives the ultrasound probe 10 to perform the disengagement motion, calculates a reset motion parameter that corresponds to the opposite direction of the disengagement motion parameter, and then controls the drive mechanism 30 to drive the ultrasound probe 10 to perform the reset motion based at least on the reset motion parameter. It should be understood that the two motion parameters being opposite means that when one motion parameter dictates the movement of the ultrasound probe 10 in one direction by a first scalar (displacement or angle, etc.), the other motion parameter that is opposite to it can dictate the movement of the ultrasound probe 10 by the same first scalar in the direction that is opposite to said one direction.

Accordingly, in some embodiments, the controller 90 controls the drive mechanism 30 to drive the ultrasound probe 10 to perform the reset motion based at least on the reset motion parameter. In some examples, the reset motion parameter may be calculated based on the disengagement motion parameter and/or the real-time ultrasound image.

The above are some descriptions of the second function key 92.

In some embodiments, the controller 90 a pressure exerted on the ultrasound probe 10, or the contact force between the ultrasound probe 10 and the biological tissue. There are various ways to achieve this, as detailed below.

Figure 13:
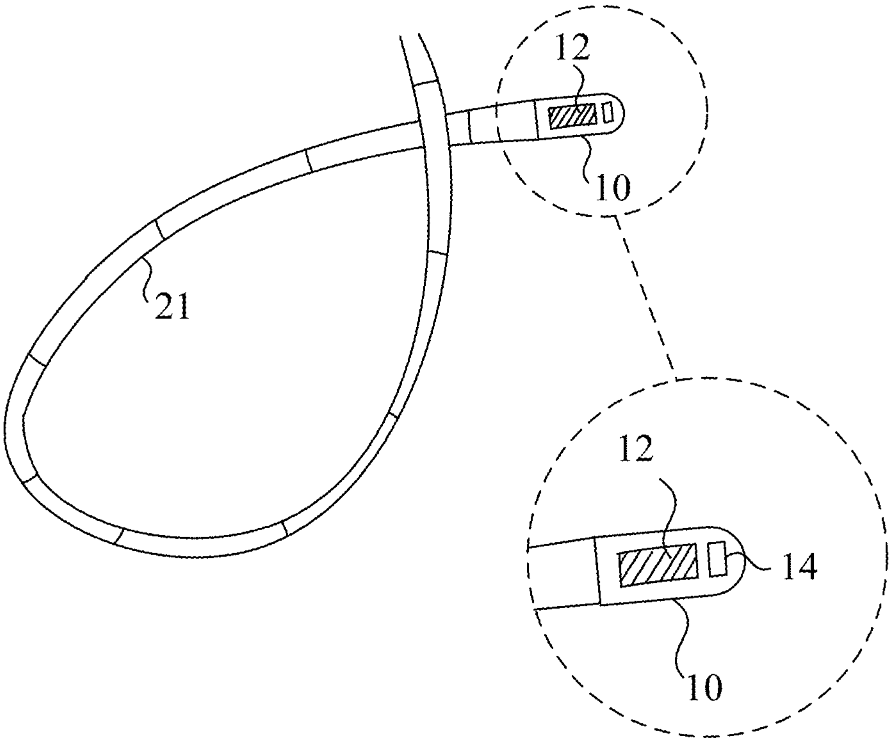
FIG. 13 is a schematic diagram of an ultrasound probe equipped with a pressure sensor in some embodiments.

In some embodiments, the ultrasound probe 10 is also equipped with a pressure sensor 14, as shown in FIG. 13. The pressure sensor 14 is configured to convert a sensed pressure into an electrical signal to measure the contact force between the ultrasound probe 10 and the biological tissue. For example, the pressure sensor 14 may be a piezoresistive pressure sensor, a ceramic pressure sensor, a diffused silicon pressure sensor, a piezoelectric pressure sensor, or the like.

In some embodiments, the controller 90 may calculate the contact force between the ultrasound probe 10 and the biological tissue based on the ultrasound image. For example, the controller 90 may extract image features of the real-time ultrasound image, and map the image features to the contact force (or pressure) between the ultrasound probe 10 and the biological tissue. Image features may be represented by one or more vectors and may be statistical features, such as but not limited to average gray level, contrast, etc. Image features may also be extracted using manually designed filters, including but not limited to one-dimensional, two-dimensional, or temporal filters. Additionally, image features may be extracted using machine learning algorithms, such as those based on convolutional deep learning networks or self-attention mechanisms. Image features may also be a combination of the aforementioned types. The methods for mapping image features to the pressure may include manually calibrated mapping relationships, manually designed mapping algorithms, or machine learning-based mapping algorithms.

In some examples, the controller 90 extracts an image of a shallow tissue from the ultrasound image, determines the deformation of the shallow tissue in a depth range of ultrasound imaging based on the shallow tissue images, and calculates the contact force based on the deformation. Generally, the greater the deformation, the greater the contact force.

In some examples, the controller 90 may determine whether the ultrasound probe 10 and the biological tissue are in the contact state or the non-contact state based on the contact force. For example, when the contact force is greater than zero, it determines that the ultrasound probe 10 and the biological tissue are in the contact state; and when the contact force is zero, it determines that the ultrasound probe 10 and the biological tissue are in the non-contact state.

In some examples, considering safety issues, the controller 90 may monitor the contact force (or pressure) between the ultrasound probe 10 and the biological tissue in real time. The controller 90 may send instructions to the drive mechanism 30 at a certain frequency, including the movement direction and speed for driving the ultrasound probe 10, so that the ultrasound probe 10 is driven to move in the corresponding direction and speed. The controller 90 may calculate the specific amount of movement in each direction, including both linear displacement and rotation angle, in real-time, and monitor the contact force (or pressure) between the ultrasound probe 10 and the biological tissue. When the amount of movement, such as the displacement and/or rotation angle, reaches the maximum value, or when the pressure exceeds a predetermined safety threshold, the controller 90 may send a stop movement instruction to the drive mechanism 30, causing the ultrasound probe 10 to stop moving.

Accordingly, in some examples, the controller 90 obtains the contact force and determines whether the contact force is greater than the first predetermined pressure threshold (e.g. the aforesaid safety threshold). If the contact force is greater than the first predetermined pressure threshold, the controller controls the drive mechanism 30 to stop the movement and/or to issue an alarm. For example, during the reset motion, when the controller 90 detects that whether the contact force exceeds the first predetermined pressure threshold, it controls the drive mechanism 30 to stop the movement of the ultrasound probe 10.

In the present disclosure, the ultrasound probe 10 may be a transesophageal echocardiography (TEE probe) 10; the body cavity may be an esophagus or stomach; and the guide body 21 is configured to guide the TEE probe 10 at the distal portion 23 into a patient's esophagus or stomach. Accordingly, when the TEE probe 10 is guided into the patient's esophagus or stomach and is in the contact state with the inner wall tissue of the esophagus or stomach, the TEE probe 10 performs the transmission of ultrasound waves to the heart and the reception of ultrasound echoes to obtain ultrasound echo signals, wherein the ultrasound echo signals are used to generate a transesophageal echocardiogram. The triggering of the first function key 91 by the operator enables the TEE probe 10 to be transitioned from the contact state with the inner wall tissue of the esophagus or stomach to the non-contact state; and then the triggering of the second function key 92 by the operator enables the TEE probe 10 to be transitioned from the non-contact state with the inner wall tissue of the esophagus or stomach to the contact state.

An ultrasound imaging method is also disclosed in some embodiments. In some examples, the ultrasound imaging method may be applied to the ultrasound device 100 in some embodiments of the present disclosure.

Figure 14:
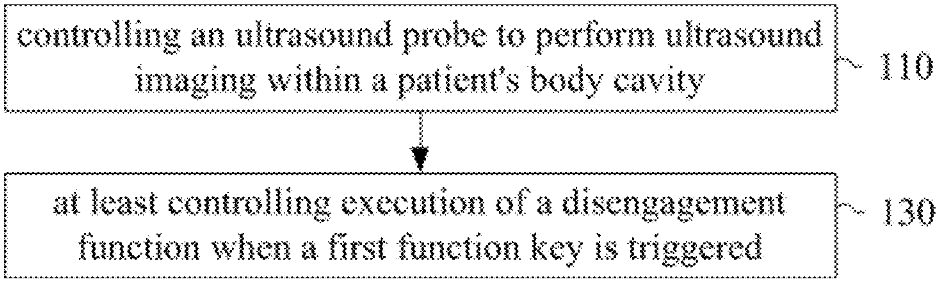
FIG. 14 is a flowchart of an ultrasound imaging method in some embodiments.

Referring to FIG. 14, the ultrasound imaging method in some embodiments may include the following steps:

Step 110: controlling an ultrasound probe 10 to perform ultrasound imaging within a patient's body cavity. Specifically, step 110 involves controlling the ultrasound probe 10 to perform the transmission of ultrasound waves and the reception of ultrasound echoes to obtain ultrasound echo signals that are used to generate an ultrasound image, wherein the ultrasound probe 10 is guided into the body cavity and is in the contact state with the biological tissue of the body cavity.

Step 130: at least controlling execution of a disengagement function when a first function key 91 is triggered, wherein the disengagement function comprises controlling the ultrasound probe 10 to perform the disengagement motion so as to transition from the contact state to the non-contact state with the biological tissue.

In some embodiments, when the first function key 91 is triggered, step 130 involves not only performing the disengagement function but also controlling execution of a first function and/or a stop transmission-reception function.

The following is a description of the functions associated with the first function key 91.

In some embodiments, the disengagement function comprises: controlling the ultrasound probe 10 to perform the disengagement motion so as to transition from the contact state to the non-contact state with the biological tissue.

In some examples, the disengagement motion comprise: a backward motion of the ultrasound probe 10 in a front-rear direction defined by the front side 11 and the rear side 13. In some examples, the backward motion comprises a linear and/or rotational backward movement of the ultrasound probe 10 in the front-rear direction defined by the front side 11 and the rear side 13.

In some examples, the disengagement motion has a first movement range that comprises a first linear displacement and/or a first angular rotation so as to transition the ultrasound probe 10 from the contact state to the non-contact state with the biological tissue when performing the disengagement motion.

In some examples, the stop transmission-reception function comprises: controlling the ultrasound probe 10 to stop the transmission of ultrasound waves and the reception of ultrasound echoes.

In some examples, the first function is different from the disengagement function.

In some examples, the first function is distinct from a function for driving the movement of the ultrasound probe 10. In other examples, the first function is independent of the function for driving the movement of the ultrasound probe 10. In still other examples, the first function excludes the function for driving the movement of the ultrasound probe 10.

In some examples, the first function differs from the stop transmission-reception function.

In some examples, the first function is to freeze ultrasound images; and correspondingly, the first function key 91 may be configured as a freeze key. That is, the first function key 91 can serve as the freeze key, sharing the function of the original freeze key in the ultrasound device 100. When the function to freeze the ultrasound images is activated, the controller 90 may also control the execution of the disengagement function. In some examples, the original freeze key in the ultrasound device 100 not only freezes the ultrasound images but also causes the ultrasound probe 10 to stop the transmission of ultrasound waves and the reception of ultrasound echoes; consequently, when the freeze key is triggered, in step 130, there only needs to additionally control the execution of the disengagement function. In other examples, the freeze function implemented by the original freeze key only freezes the ultrasound image without causing the ultrasound probe 10 to stop the transmission of ultrasound waves and the reception of ultrasound echoes; consequently, when the freeze key is triggered, step 130 may further involve controlling the execution of the disengagement function and, optionally, the stop transmission-reception function. Furthermore, the first function key 91 and the original freeze key in the ultrasound device 100 can be two separate keys, wherein when the original freeze key is triggered, it can either freeze the ultrasound images, or freeze the ultrasound images and cause the ultrasound probe 10 to stop the transmission of ultrasound waves and the reception of ultrasound echoes; and when the first function key 91 is triggered, it can execute the disengagement function and the freeze function, or it can execute the disengagement function, the freeze function and the stop transmission-reception function.

In some examples, the first function is to switch from the operative mode to the sleep mode; correspondingly, the first function key 91 may be configured as a sleep key. That is, the first function key 91 can serve as the sleep key, sharing the function of the original sleep key in the ultrasound device 100. When the sleep function (i.e., switching the operative mode of the ultrasound device 100 to the sleep mode) is activated, step 130 may also involve controlling the execution of the disengagement function. In some examples, the original sleep key in the ultrasound device 100 may include allowing the ultrasound probe 10 to stop the transmission of ultrasound waves and the reception of ultrasound echoes; consequently, when the sleep key is triggered, in step 130, there only needs to additionally control the execution of the disengagement function. Furthermore, the first function key 91 and the original sleep key in the ultrasound device 100 may be two separate keys, wherein when the original sleep key in the ultrasound device 100 is triggered, it can activate the sleep function; and when the first function key 91 is triggered, it can execute the disengagement function and the sleep function, or it can execute the disengagement function, the sleep function and the stop transmission-reception function.

In some embodiments, the first function is to switch from the operative mode to the locked mode; and correspondingly, the first function key 91 may be configured as a lock key. That is, the first function key 91 can serve as the lock key, sharing the function of the original lock key in the ultrasound device 100. When the function to lock (i.e., switching the operative mode of the ultrasound device 100 to the locked mode) is activated, step 130 may also involve controlling the execution of the disengagement function. In some examples, the lock function realized by the original lock key in the ultrasound device 100 may or may not include the function of causing the ultrasound probe 10 to stop the transmission of ultrasound waves and the reception of ultrasound echoes; consequently, when the sleep key is triggered, in step 130, there at least needs to additionally control the execution of the disengagement function. Furthermore, the first function key 91 and the original lock key in the ultrasound device 100 may also be two separate keys; wherein the lock function may be executed when the original lock key in the ultrasound device 100 is triggered; and when the first function key 91 is triggered, it can execute the disengagement function and the lock function, or it can execute the disengagement function, the lock function and the stop transmission-reception function.

In some embodiments, the first function is to save a current ultrasound image; and correspondingly, the first function key 91 may be configured as a save key. That is, the first function key 91 can serve as the save key, sharing the function of the original save key in the ultrasound device 100. When executing saving the current ultrasound image, step 130 may also involve controlling the execution of the disengagement function, or step 130 may also involve controlling the execution of the disengagement function and the stop transmission-reception function. Furthermore, the first function key 91 and the original save key in the ultrasound device 100 may also be two separate keys; wherein when the original save key in the ultrasound device 100 is triggered, the function of saving the current ultrasound image may be executed; and when the first function key 91 is triggered, it can execute the function of saving the current ultrasound image and the disengagement function, or it can execute the function of saving the current ultrasound image, the disengagement function, and the stop transmission-reception function.

In some examples, the triggering of the first function key 91 may be a first type, such as a short press. In some examples, the first function key 91 may also be triggered upon being pressed or upon being released after being pressed. The first function key 91 may not cause the ultrasound device 100 to perform different functions or actions based on the duration of the press.

Figure 15:
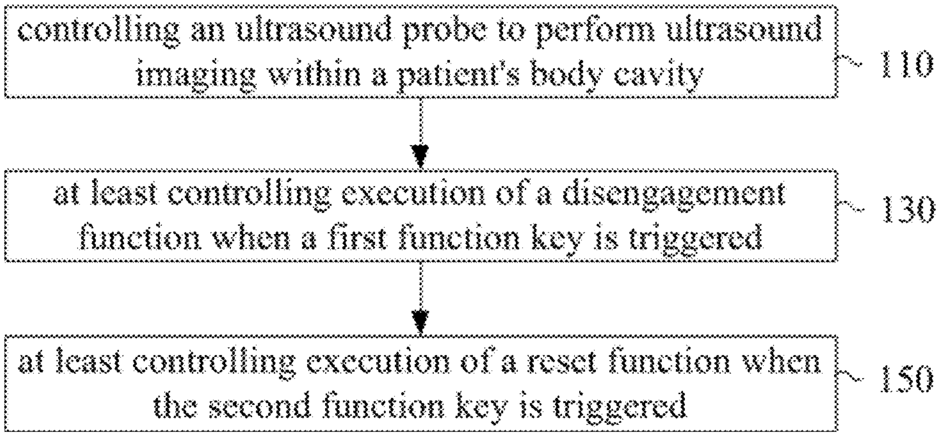
FIG. 15 is a flowchart of an ultrasound imaging method in some embodiments.

Referring to FIG. 15, the ultrasound imaging method in some embodiments may also include step 150, i.e., at least controlling execution of a reset function when the second function key 92 is triggered. In some embodiments, when the second function key 92 is triggered, step 150 involves not only performing the reset function but also controlling execution of a second function and/or a transmission-reception function.

The following is a description of the functions associated with the second function key 92.

In some embodiments, the reset function comprises: controlling the ultrasound probe 10 perform the reset motion so as to transition from the non-contact state to the contact state with the biological tissue.

In some examples, the reset motion comprises a forward motion of the ultrasound probe 10 in the front-rear direction defined by the front side 11 and the rear side 13. In some examples, the forward motion comprises a linear and/or rotational forward movement of the ultrasound probe 10 in the front-rear direction defined by the front side 11 and the rear side 13.

In some examples, the transmission-reception function comprises controlling the ultrasound probe 10 to resume the transmission of ultrasound waves and the reception of ultrasound echoes.

In some examples, the second function is different from the reset function.

In some examples, the second function is different from the function for driving the ultrasound probe 10. In some examples, the second function is independent of the function for driving the ultrasound probe 10. In some examples, the second function excludes the function for driving the ultrasound probe 10.

In some examples, the second function is different from the transmission-reception function.

In some examples, the second function is contrary to or serves as a function opposite to the first function. For example, the first function is to freeze ultrasound images, and the second function is to unfreeze the ultrasound images. For another example, the first function is to switch from the operative mode to the sleep mode, and the second function is to switch from the sleep mode to the operative mode. For yet another example, the first function is to switch from the operative mode to the locked mode, and the second function is to switch from the locked mode to the operative mode. The following is a detailed explanation.

In some examples, the second function is to unfreeze ultrasound images; and correspondingly, the second function key 92 may be an unfreeze key. That is, the second function key 92 can serve as the unfreeze key, sharing the function of the original unfreeze key in the ultrasound device 100. When the function to unfreeze ultrasound images is activated, step 150 may also involve controlling the execution of the reset function. In some examples, besides unfreezing the ultrasound images, the original unfreeze key in the ultrasound device 100 may also allow the ultrasound probe 10 to resume the transmission of ultrasound waves and the reception of ultrasound echoes; consequently, when the unfreeze key is triggered, in step 150, there only needs to additionally control the execution of the reset function. In some examples, the unfreeze function implemented by the original unfreeze key only unfreezes the ultrasound image without causing the ultrasound probe 10 to resume the transmission of ultrasound waves and the reception of ultrasound echoes; consequently, when the unfreeze key is triggered, step 150 may further involve controlling the execution of the reset function and, optionally, the transmission-reception function. Furthermore, the second function key 92 and the original unfreeze key in the ultrasound device 100 can be two separate keys, wherein when the original unfreeze key is triggered, it can either unfreeze the ultrasound images, or unfreeze the ultrasound images and cause the ultrasound probe 10 to resume performing the transmission of ultrasound waves and reception of ultrasound echoes; and when the second function key 92 is triggered, it can execute the reset function and the unfreeze function, or it can execute the reset function, the unfreeze function and the transmission-reception function.

In some examples, the second function is to switch from the sleep mode to the operative mode; and correspondingly, the second function key 92 may be a wake-up key. That is, the second function key 92 is the wake-up key, sharing the function of the original wake-up key in the ultrasound device 100. When the wake-up function (i.e., switching the ultrasound device 100 from the sleep mode to the operative mode) is activated, step 150 may further involve controlling the execution of the reset function. In some examples, the wake-up function implemented by the original wake-up key in the ultrasound device 100 may or may not include the function for allowing the ultrasound probe 10 to perform the transmission of ultrasound waves and the reception of ultrasound echoes; consequently, when the wake-up key is triggered, in step 150, there may at least need to additionally further control the execution of the reset function. Furthermore, the second function key 92 and the original wake-up key in the ultrasound device 100 may be two separate keys, wherein when the original wake-up key in the ultrasound device 100 is triggered, the wake-up function may be executed; and when the second function key 92 is triggered, it can execute the reset function and the wake-up function, or it can execute the reset function, the wake-up function and the transmission-reception function.

In some examples, the second function is to switch from the locked mode to the operative mode; and correspondingly, the second function key 92 may be configured as an unlock key. That is, the second function key 92 may serve as an unlock key, sharing the function of the original unlock key in the ultrasound device 100. When the unlock function (i.e., switching the ultrasound device 100 from the operative mode to unlock mode) is activated, step 150 may also involve controlling the execution of the reset function. In some examples, the unlock function realized by the original unlock key in the ultrasound device 100 may or may not include the function for allowing the ultrasound probe 10 to perform the transmission of ultrasound waves and the reception of ultrasound echoes; and accordingly, when the unlock key is triggered, in step 150, there may at least additionally further control the execution of the reset function. Furthermore, the second function key 92 and the original unlock key in the ultrasound device 100 may be two separate keys, wherein when the original unlock key is triggered, the unlock function may be executed; and when the second function key 92 is triggered, it may execute the reset function and the unlock function, or it can execute the reset function, the unlock function and the transmission-reception function.

The restoring of the ultrasound probe 10 from disengagement can be realized via the second function key 92 by the operator. In some embodiments, step 150 involves controlling the drive mechanism 30 to drive the ultrasound probe 10 to perform the reset motion until the ultrasound probe 10 reaches a predetermined position. In some examples, the predetermined position may include any one of the following:

(1) an initial position of the ultrasound probe 10 relative to the biological tissue before performing the disengagement motion;

(2) a position of the ultrasound probe where a similarity between an ultrasound image of said position and a predetermined sectional image is greater than a predetermined similarity threshold;

(3) a position of the ultrasound probe where the quality metric of the generated ultrasound image is greater than a predetermined quality threshold;

(4) a position of the ultrasound probe where both a similarity between an ultrasound image of said position and a predetermined sectional image is greater than a predetermined similarity threshold, and a quality metric of the ultrasound image is greater than a predetermined quality threshold; and (5) a position of the ultrasound probe where the contact force between the ultrasound probe 10 and the biological tissue satisfied a predetermined pressure condition.

In some examples, step 150 may involve controlling the ultrasound probe 10 to perform the reset motion based on the real-time ultrasound images.

For example, in step 150, based at least on the real-time ultrasound images, the drive mechanism 30 is controlled to drive the ultrasound probe to perform the reset motion so as to move to a predetermined position, such as any one of the aforementioned positions (1) to (5). In some examples, step 150 involves calculating a reset motion parameter based on at least one pre-stored target ultrasound image and the real-time ultrasound images, and controlling the drive mechanism 30 based at least on the reset motion parameter to drive the ultrasound probe 10 to perform the reset motion. The at least one pre-stored target ultrasound image may include an ultrasound image captured by the ultrasound probe 10 at the initial position, or, a plurality of ultrasound images of different sections captured by the ultrasound probe 10 within a predetermined range while controlled by the controller 90 prior to performing the disengagement motion.

In some examples, step 150 involves obtaining the disengagement motion parameter that drives the ultrasound probe 10 to perform the disengagement motion, calculating a reset motion parameter that corresponds to the opposite direction of the disengagement motion parameter, and then controlling the ultrasound probe 10 to perform the reset motion based at least on the reset motion parameter.

Accordingly, in some embodiments, step 150 involves controlling the ultrasound probe 10 to perform the reset motion based at least on the reset motion parameter. In some examples, the reset motion parameter may be calculated based on the disengagement motion parameter and/or the real-time ultrasound image.

The present disclosure refers to various exemplary embodiments for illustrative purposes. However, those skilled in the art will recognize that modifications and alterations may be made to these embodiments without departing from the scope of the disclosure. For instance, individual operational steps and components for performing such steps may be implemented in diverse manners depending on specific applications or considerations of cost functions associated with system operations (e.g., one or more steps may be deleted, modified, or consolidated with other steps).

The embodiments described herein may be implemented in whole or in part through software, hardware, firmware, or any combination thereof. Moreover, as understood by those skilled in the art, the principles disclosed may be embodied in a computer program product stored on a non-transitory computer-readable storage medium preloaded with computer-readable program code. Any tangible, non-transitory computer-readable storage medium may be utilized, including but not limited to: magnetic storage devices (e.g., hard disks, floppy disks); optical storage devices (e.g., CD-ROMs, DVDs, Blu-ray discs); and flash memory devices. The computer program instructions may be loaded onto a general-purpose computer, special-purpose computer, or other programmable data processing apparatus to create a machine, such that the instructions executed on the computer or programmable apparatus produce means for implementing specified functions. These instructions may also reside in a computer-readable memory, directing the computer or programmable apparatus to operate in a defined manner, thereby forming an article of manufacture comprising functional implementation means. Furthermore, the computer program instructions may be executed on a computer or programmable data processing apparatus to generate a computer-implemented process, wherein the executed instructions provide steps for realizing the specified functionality, including but not limited to: technical improvements in data processing efficiency (e.g., optimized memory allocation); and enhanced accuracy in algorithmic execution (e.g., reduced error margins in machine learning models).

While the principles disclosed herein have been illustrated through various embodiments, it should be understood that structural configurations, material selections, and component proportions particularly suited to specific operational environments may be modified without departing from the scope and spirit of the disclosure. Such modifications, along with other adaptations or adjustments, shall be encompassed within the scope of the present disclosure.

The foregoing detailed description has been described with reference to various embodiments. However, those skilled in the art will recognize that modifications and variations may be made without departing from the scope of the disclosure. Accordingly, the description of the disclosure shall be interpreted in an illustrative rather than restrictive sense, and all such modifications are intended to be included within its scope. Similarly, discussions of advantages, alternative solutions to problems, and operational benefits associated with the embodiments are provided above. Nevertheless, benefits, advantages, solutions to problems, and any elements that may produce such effects or render them more explicit shall not be construed as critical, required, or essential. Furthermore, the term 'coupled' and its derivatives encompass physical connections (e.g., mechanical joints), electrical connections (e.g., circuit interconnects), magnetic linkages (e.g., inductive coupling), optical interfaces (e.g., fiber-optic alignment), communication channels (e.g., wireless protocols), functional integrations (e.g., software APIs), and any other form of association that achieves operational interaction.

Those skilled in the art will recognize that numerous modifications to the details of the above-described embodiments may be made without departing from the fundamental principles of the disclosed subject matter. Accordingly, the scope of the present disclosure shall be determined solely by the claims and their legal equivalents.

The invention claimed is:

1. An ultrasound device, comprising:
an ultrasound probe, configured to perform transmission of ultrasound waves and reception of ultrasound echoes to obtain ultrasound echo signals;
a guidance member, comprising a guide body and a distal portion, wherein the ultrasound probe is disposed at the distal portion, and the guide body is configured to guide the ultrasound probe at the distal portion into a patient's body cavity;
a drive mechanism, configured to drive the ultrasound probe to move within the body cavity;
a first function key, capable of being triggered by an operator to execute a first function; and
a controller; wherein:
when the ultrasound probe is guided into the body cavity and is in a contact state with a biological tissue that forms the body cavity, the ultrasound probe is configured to perform the transmission of ultrasound waves and the reception of ultrasound echoes to obtain the ultrasound echo signals that are used to generate an ultrasound image; and
when the first function key is triggered, the controller is configured to control execution of the first function and a disengagement function; wherein the first function is different from the disengagement function, and the disengagement function comprises the controller controlling the drive mechanism to drive the ultrasound probe to perform a disengagement motion so as to transition from the contact state to a non-contact state with the biological tissue.

2. The ultrasound device according to claim 1, wherein the ultrasound probe has a front side and a rear side that is opposite to the front side, wherein the front side of the ultrasound probe comprises a contact region configured to contact the biological tissue, and the disengagement motion comprises a backward motion of the ultrasound probe in a front-rear direction defined by the front side and the rear side.

3. The ultrasound device according to claim 1, wherein when the first function key is triggered, the controller is further configured to control execution of a stop transmission-reception function, wherein the stop transmission-reception function comprises the controller controlling the ultrasound probe to stop the transmission of ultrasound waves and the reception of ultrasound echoes.

4. The ultrasound device according to claim 1, wherein when the first function key is triggered, the controller is further configured to determine whether the ultrasound probe is in the contact state with the biological tissue:
when the ultrasound probe is in the contact state with the biological tissue, the controller is further configured to execute the disengagement function; and
when the ultrasound probe is in the non-contact state with the biological tissue, the controller is further configured to prohibit the execution of the disengagement function.

5. The ultrasound device according to claim 1, wherein the first function key is any one of the following:
a freeze key, wherein the first function is to freeze the ultrasound image;
a sleep key, wherein the first function is to switch from an operative mode to a sleep mode;
a lock key, wherein the first function is to switch from the operative mode to a locked mode; and
a save key, wherein the first function is to save the ultrasound image.

6. The ultrasound device according to claim 1, further comprising a second function key;
wherein when the second function key is triggered by the operator, the controller is further configured to control execution of a reset function; wherein the reset function comprises the controller controlling the drive mechanism to drive the ultrasound probe to perform a reset motion so as to transition from the non-contact state to the contact state with the biological tissue.

7. The ultrasound device according to claim 6, wherein when the second function key is triggered by the operator, the controller is further configured to control execution of a transmission-reception function, wherein the transmission-reception function comprises the controller controlling the ultrasound probe to resume the transmission of ultrasound waves and the reception of ultrasound echoes.

8. The ultrasound device according to claim 6, wherein when the second function key is triggered, the controller is further configured to control execution of a second function, wherein the second function is different from the reset function.

9. The ultrasound device according to claim 8, wherein the second function key is any one of the following:
an unfreeze key, wherein the second function is to unfreeze the ultrasound image;
a wake-up key, wherein the second function is to switch from a sleep mode to an operative mode; and
an unlock key, wherein the second function is to switch from a locked mode to an operative mode.

10. The ultrasound device according to claim 6, wherein the controller controlling the drive mechanism to drive the ultrasound probe to perform the reset motion so as to transition from the non-contact state to the contact state with the biological tissue, comprises:

the controller controlling the drive mechanism to drive the ultrasound probe to perform the reset motion until the ultrasound probe reaches a predetermined position; wherein the predetermined position comprises any one of the following:

an initial position of the ultrasound probe relative to the biological tissue before performing the disengagement motion;

a position of the ultrasound probe where a similarity between an ultrasound image of said position and a predetermined sectional image is greater than a predetermined similarity threshold;

a position of the ultrasound probe where a quality metric of the ultrasound image is greater than a predetermined quality threshold;

a position of the ultrasound probe where both a similarity between an ultrasound image of said position and a predetermined sectional image is greater than a predetermined similarity threshold, and a quality metric of the ultrasound image is greater than a predetermined quality threshold; and a position of the ultrasound probe where a contact force between the ultrasound probe and the biological tissue satisfies a predetermined pressure condition.

11. The ultrasound device according to claim 10, wherein the controller controlling the drive mechanism to drive the ultrasound probe to perform the reset motion until the ultrasound probe reaches the predetermined position, comprises:

the controller determining whether the ultrasound probe has moved to the initial position based on a real-time ultrasound image and at least one pre-stored target ultrasound image;

wherein the at least one pre-stored target ultrasound image comprises:

an ultrasound image captured by the ultrasound probe at the initial position; or a plurality of ultrasound images on different sections captured by the ultrasound probe while controlled by the controller to move within a predetermined range prior to performing the disengagement motion.

12. The ultrasound device according to claim 10, wherein the controller controlling the drive mechanism to drive the ultrasound probe to perform the reset motion until the ultrasound probe reaches the predetermined position, further comprises:

the controller controlling the drive mechanism to drive the ultrasound probe to perform the reset motion so as to move to the predetermined position based at least on the real-time ultrasound image, wherein the controller is further configured to calculate a reset motion parameter based on the at least one pre-stored target ultrasound image and the real-time ultrasound image, and to control the drive mechanism to drive the ultrasound probe to perform the reset motion based at least on the reset motion parameter;

wherein the at least one pre-stored target ultrasound image comprises:

an ultrasound image captured by the ultrasound probe at the initial position; or a plurality of ultrasound images on different sections captured by the ultrasound probe while controlled by the controller to move within a predetermined range prior to performing the disengagement motion.

13. The ultrasound device according to claim 6, wherein the controller controlling the drive mechanism to drive the ultrasound probe to perform the reset motion so as to transition from the non-contact state to the contact state with the biological tissue, comprises:

the controller obtaining a disengagement motion parameter of the drive mechanism during the disengagement motion of the ultrasound probe, and calculating to obtain a reset motion parameter that is opposite to the disengagement motion parameter; and the controller controlling the drive mechanism to drive the ultrasound probe to perform the reset motion based at least on the reset motion parameter.

14. The ultrasound device according to claim 1, wherein the ultrasound probe is further provided with a pressure sensor that is configured to convert a detected pressure into electrical signals for measuring a contact force between the ultrasound probe and the biological tissue;

or, the controller is further configured to calculate a contact force between the ultrasound probe and the biological tissue based on the ultrasound image.

15. The ultrasound device according to claim 14, wherein the controller calculating the contact force between the ultrasound probe and the biological tissue based on the ultrasound image, comprises:

the controller extracting an image of a shallow tissue from the ultrasound image, determining a deformation of the shallow tissue in a depth range of ultrasound imaging based on the shallow tissue image, and calculating the contact force based on the deformation.

16. The ultrasound device according to claim 1, wherein the ultrasound probe is a transesophageal echocardiography (TEE) probe;

the body cavity is an esophagus or a stomach of the patient; and the guide body is configured to guide the TEE probe disposed at the distal portion into the esophagus or the stomach;

wherein, when the TEE probe is guided into the esophagus or the stomach and is in the contact state with an inner wall tissue of the esophagus or the stomach, the TEE probe is configured to transmit the ultrasound waves to a heart of the patient and receive the ultrasound echoes to obtain the ultrasound echo signals that are used to generate a transesophageal echocardiogram.

17. An ultrasound device, comprising:

an ultrasound probe, configured to perform transmission of ultrasound waves and reception of ultrasound echo signals;

a guidance member, comprising a guide body and a distal portion, wherein the ultrasound probe is disposed at the distal portion, and the guide body is configured to guide the ultrasound probe at the distal portion into a patient's body cavity;

a drive mechanism, configured to drive the ultrasound probe to move within the body cavity;

one first function key, capable of being triggered in a first type by an operator to execute a disengagement function; and a controller; wherein:

when the ultrasound probe is guided into the body cavity and in a contact state with a biological tissue that forms the body cavity, the ultrasound probe performs the transmission of ultrasound waves and the reception of ultrasound echoes to obtain the ultrasound echo signals that are used to generate an ultrasound image; and when the first function key is triggered in the first type, the controller is configured to control execution of the disengagement function, wherein the disengagement function comprises the controller controlling the drive mechanism to drive the ultrasound probe to perform a disengagement motion, so as to transition from the contact state to a non-contact state with the biological tissue.

18. The ultrasound device according to claim 17, wherein the first-type trigger is a short press.

19. The ultrasound device according to claim 17, further comprising a second function key; wherein when the second function key is triggered by the operator, the controller is further configured to control execution of a reset function, wherein the reset function comprises the controller controlling the drive mechanism to drive the ultrasound probe to perform a reset motion, so as to transition from the non-contact state to the contact state with the biological tissue.

20. An ultrasound imaging method, comprising:

controlling an ultrasound probe to perform transmission of ultrasound waves and reception of ultrasound echoes to obtain ultrasound echo signals that are used to generate an ultrasound image, wherein the ultrasound probe is guided into a patient's body cavity and is in a contact state with a biological tissue that forms the body cavity; and controlling execution of a first function and a disengagement function when a first function key is triggered, wherein the first function is different from the disengagement function, wherein the disengagement function comprises: controlling the ultrasound probe to perform a disengagement motion so as to transition from the contact state to a non-contact state with the biological tissue.

* * * * *